US008617592B2

(12) United States Patent
Jiang et al.

(10) Patent No.: US 8,617,592 B2
(45) Date of Patent: Dec. 31, 2013

(54) SELF-ASSEMBLED PARTICLES FROM ZWITTERIONIC POLYMERS AND RELATED METHODS

(75) Inventors: Shaoyi Jiang, Redmond, WA (US); Zhiqiang Cao, Somerville, MA (US); Hong Xue, Pleasanton, CA (US); Lei Zhang, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 13/463,662

(22) Filed: May 3, 2012

(65) Prior Publication Data

US 2012/0259021 A1 Oct. 11, 2012

Related U.S. Application Data

(63) Continuation of application No. PCT/US2010/055887, filed on Nov. 8, 2010.

(60) Provisional application No. 61/259,085, filed on Nov. 6, 2009.

(51) Int. Cl.
*A61K 9/127* (2006.01)
*A61K 9/107* (2006.01)

(52) U.S. Cl.
CPC .............. *A61K 9/127* (2013.01); *A61K 9/1075* (2013.01)
USPC .......................... 424/450; 514/772.1; 525/419

(58) Field of Classification Search
None
See application file for complete search history.

(56) References Cited

U.S. PATENT DOCUMENTS

| | | |
|---|---|---|
| 3,671,502 A | 6/1972 | Samour |
| 4,075,183 A | 2/1978 | Kawakami |
| 4,138,446 A | 2/1979 | Kawakami |
| 4,415,388 A | 11/1983 | Korpman |
| 4,493,926 A | 1/1985 | Williams, Jr. |
| 4,985,023 A | 1/1991 | Blank |
| 5,204,060 A | 4/1993 | Allenmark |
| 5,714,360 A | 2/1998 | Swan |
| 5,919,523 A | 7/1999 | Sundberg |
| 5,986,042 A | 11/1999 | Irizato |
| 6,361,768 B1 | 3/2002 | Galleguillos |
| 6,486,333 B1 | 11/2002 | Murayama |

(Continued)

FOREIGN PATENT DOCUMENTS

DE  10 2006 004 111 A1  8/2007
EP        0 354 984 A2   2/1990

(Continued)

OTHER PUBLICATIONS

SM Berge, LD Bighley, DC Monkhouse. "Pharmaceutical Salts." Journal of Pharmaceutical Sciences, vol. 66 No. 1, Jan. 1977, pp. 1-19.*

(Continued)

*Primary Examiner* — Frederick Krass
*Assistant Examiner* — Isaac Shomer
(74) *Attorney, Agent, or Firm* — Christensen O'Connor Johnson Kindness PLLC

(57) ABSTRACT

Zwitterionic block copolymers and zwitterionic conjugates that advantageously self-assemble into particles, particles assembled from the zwitterionic block copolymers and zwitterionic conjugates, pharmaceutical compositions that include the self-assembled particles, and methods for delivering therapeutic and diagnostic agents using the particles.

9 Claims, 13 Drawing Sheets

(56) References Cited

U.S. PATENT DOCUMENTS

| | | | |
|---|---|---|---|
| 6,897,263 | B2 | 5/2005 | Hell |
| 7,056,532 | B1 | 6/2006 | Kabanov |
| 7,291,427 | B2 | 11/2007 | Kawamura |
| 7,306,625 | B1 | 12/2007 | Stratford |
| 7,335,248 | B2 | 2/2008 | Abou-Nemeh |
| 7,737,224 | B2 | 6/2010 | Willis |
| 2004/0063881 | A1 | 4/2004 | Lewis |
| 2005/0058689 | A1 | 3/2005 | McDaniel |
| 2006/0183863 | A1* | 8/2006 | Huang et al. ............... 525/234 |
| 2006/0240072 | A1 | 10/2006 | Chudzik |
| 2007/0042198 | A1 | 2/2007 | Schonemyr |
| 2007/0104654 | A1 | 5/2007 | Hsieh |
| 2008/0131393 | A1 | 6/2008 | Yeung |
| 2008/0181861 | A1* | 7/2008 | Jiang et al. ............... 424/78.09 |
| 2008/0299177 | A1 | 12/2008 | Hardy |
| 2009/0197791 | A1 | 8/2009 | Balastre |

FOREIGN PATENT DOCUMENTS

| | | |
|---|---|---|
| EP | 0 419 654 A1 | 4/1991 |
| EP | 0 479 245 A2 | 4/1992 |
| JP | 63-234007 A | 9/1988 |
| RU | 1780673 A1 | 12/1992 |
| WO | 00/39176 A1 | 7/2000 |
| WO | 2004/058837 A2 | 7/2004 |
| WO | 2004/100666 A1 | 11/2004 |
| WO | 2007/068744 A1 | 6/2007 |
| WO | 2007/099239 A2 | 9/2007 |

OTHER PUBLICATIONS

Chang, Y., et al., "Highly Protein-Resistant Coatings From Well-Defined Diblock Copolymers Containing Sulfobetaines," Langmuir 22(5):2222-2226, Feb. 2006.

Chen, S., et al., "Controlling Antibody Orientation on Charged Self-Assembled Monolayers," Langmuir 19(7):2859-2864, Apr. 2003.

Chen, S., et al., "Strong Resistance of Oligo(phosphorylcholine) Self-Assembled Monolayers to Protein Adsorption," Langmuir 22(6):2418-2421, Mar. 2006.

Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.

Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.

Feng., W., et al., "Atom-Transfer Radical Grafting Polymerization of 2-Methacryloyloxyethyl Phosphorylcholine From Silicon Wafer Surfaces,"Journal of Polymer Science: Part A: Polymer Chemistry 42(12):2931-2942, Jun. 2004.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Lowe, A.B., et al., "Well-Defined Sulfobetaine-Based Statistical Copolymers as Potential Antibioadherent Coatings," Journal of Biomedical Materials Research 52(1):88-94, Jul. 2000.

West, S.L., et al., "The Biocompatibility of Crosslinkable Copolymer Coatings Containing Sulfobetaines and Phosphobetaines," Biomaterials 25:1195-1204, Apr. 2004.

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53(1):121-126, Jan. 2004.

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zhang, Z., et al., "Superflow Fouling Sulfobetaine and Carboxybetaine Polymers on Glass Slides," Langmuir 22(24):10072-10077, Nov. 2006.

Zhang, Z., "Surface Grafted Sulfobetaine Polymers Via Atom Transfer Radical Polymerization as Superlow Fouling Coatings," Journal of Physical Chemistry B 110(22):10799-10804, Jun. 2006.

Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization with Carboxybetaine Monomer," Colloids and Surfaces B: Biointerfaces 41(1):55-62, Mar. 2005.

"Betaine," Wikipedia, The Free Encyclopedia, <http://en.wikipedia.org/wiki/Betaine> [retrieved Jul. 31, 2011], 1 page.

"Bromide," Wikipedia, The Free Encyclopedia, <http://en.wikipedia.org/wiki/Bromide> [retrieved Jul. 27, 2011] 3 pages.

International Preliminary Report on Patentability mailed May 8, 2012, issued in corresponding International Application No. PCT/US2010/055887, filed Nov. 8, 2010, 8 pages.

International Search Report and Written Opinion mailed Jul. 28, 2011, issued in corresponding International Application No. PCT/US2010/055887, filed Nov. 8, 2010, 12 pages.

"Nail Infections," Health911, <http://www.health911.com/nail-infections> [retrieved Aug. 29, 2011], 3 pages.

* cited by examiner

SELF-ASSEMBLED PARTICLES FROM ZWITTERIONIC POLYMERS AND RELATED METHODS

CROSS-REFERENCE TO RELATED APPLICATION

This application is a continuation of International Application No. PCT/US2010/055887, filed Nov. 8, 2010, which claims the benefit of U.S. Provisional Application No. 61/259,085, filed Nov. 6, 2009, each is expressly incorporated herein by reference in its entirety.

STATEMENT OF GOVERNMENT LICENSE RIGHTS

This invention was made with Government support under Contact No. N000140910137 awarded by the Office of Naval Research, Contract No. DMR 0705907 awarded by the National Science Foundation, and Contract No. U54 CA 119335-04S awarded by the National Cancer Institute. The Government has certain rights in the invention.

BACKGROUND OF THE INVENTION

The stability and targeting efficiency of nanoparticles (NPs) are the two most important issues for their applications to drug delivery and diagnostic imaging. Coating materials are needed to render NPs both stable and multi-functional to address these two issues. Polyethylene glycol (PEG) is the material most commonly used to modify NPs for stabilization purposes due to its resistance to nonspecific protein adsorption (or nonfouling properties). However, PEG is susceptible to oxidative damage and loss of function in biological media, which limits its long-term applications. Besides their stability in complex media, the stability of NPs themselves is another important issue that is often overlooked. NPs need to remain intact throughout any necessary manufacturing processes such as centrifugation or lyophilization. To maintain the stability of NPs, including those coated with PEG, several measures must be used such as low-speed ultrafiltration and addition of cryoprotectants prior to freeze-drying. For targeting drug delivery, bio-recognition elements (e.g., targeting ligands) often need to be immobilized onto NP surfaces. There is only one functional group potentially available at the end of a long PEG chain (e.g., 2-5 kDa) to which to conjugate biomolecules. In addition, unreacted functional groups can cause non-specific binding, particularly in complex media such as blood plasma and serum. With all current NP coating materials, one will have to compromise between excellent stability and multi-functionality.

Despite the advances in the development of NP coating materials, a need exists for a single material or coating platform that can accommodate both NP ultra-stability and multi-functionality.

SUMMARY OF THE INVENTION

In one aspect, the invention provides a block copolymer, comprising:
(a) a zwitterionic polymer block comprising a poly(carboxybetaine), a poly(sulfobetaine) or a poly(phosphobetaine); and
(b) a hydrophobic block.

In one embodiment, the zwitterionic polymer block comprises a plurality of repeating units, each repeating unit having the formula:

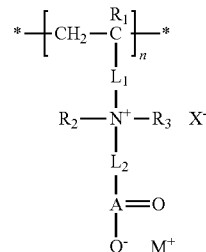

wherein
$R_1$ is selected from the group consisting of hydrogen, fluorine, trifluoromethyl, C1-C6 alkyl, and C6-C12 aryl groups;
$R_2$ and $R_3$ are independently selected from the group consisting of alkyl and aryl, or taken together with the nitrogen to which they are attached form a cationic center;
$L_1$ is a linker that covalently couples the cationic center $[N^{+}(R_2)(R_3)]$ to the polymer backbone $[-(CH_2-CR_1)_n-]$.
$L_2$ is a linker that covalently couples the anionic center $[A(=O)-O^-]$ to the cationic center;
A is C, S, SO, P, or PO;
$M^+$ is a counter ion associated with the $(A=O)O^-$ anionic center;
$X^-$ is a counter ion associated with the cationic center; and
n is an integer from 1 to about 10,000.

In another aspect, the invention provides a block copolymer, comprising:
(a) a mixed charge copolymer block comprising a mixed charge copolymer; and
(b) a hydrophobic block.

In one embodiment, the mixed charge copolymer comprises a plurality of repeating units, each repeating unit having the formula:

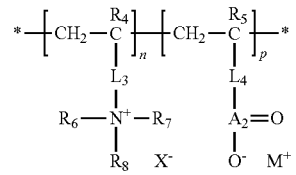

wherein
$R_4$ and $R_5$ are independently selected from hydrogen, fluorine, trifluoromethyl, C1-C6 alkyl, and C6-C12 aryl groups;
$R_6$, $R_7$, and $R_8$ are independently selected from alkyl and aryl, or taken together with the nitrogen to which they are attached form a cationic center;
$A(=O)-OM$ is an anionic center, wherein A is C, S, SO, P, or PO, and M is a metal or organic counterion;
$L_3$ is a linker that covalently couples the cationic center $[N^{+}(R_6)(R_7)(R_8)]$ to the polymer backbone;
$L_4$ is a linker that covalently couples the anionic center $[A(=O)-OM]$ to the polymer backbone;
$X^-$ is the counter ion associated with the cationic center;
n is an integer from 1 to about 10,000; and
p is an integer from 1 to about 10,000. For the above polymers, in one embodiment, the hydrophobic block comprises a biocompatible polymer. In one embodiment, the hydrophobic block comprises a homopolymer or copolymer. In one embodiment, the hydrophobic block comprises a polymer selected from the group consisting of poly(lactic-co-glycolic acid), polycaprolactone, polyglycolide, polylactic acid, poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide). In one embodiment, the hydrophobic block has a number average molecular weight from about 1,000 to about 200,000.

In one aspect, the invention provides a zwitterionic polymer conjugate, comprising a lipid covalently coupled to a poly(carboxybetaine), a poly(sulfobetaine), or a poly(phosphobetaine).

In one embodiment, the poly(carboxybetaine), poly(sulfobetaine), or poly(phosphobetaine) comprises a plurality of repeating units, each repeating unit having the formula:

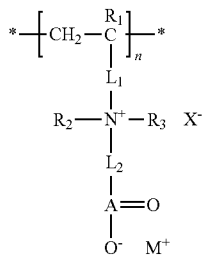

wherein $R_1$ is selected from the group consisting of hydrogen, fluorine, trifluoromethyl, C1-C6 alkyl, and C6-C12 aryl groups;

$R_2$ and $R_3$ are independently selected from the group consisting of alkyl and aryl, or taken together with the nitrogen to which they are attached form a cationic center;

$L_1$ is a linker that covalently couples the cationic center $[N^+(R_2)(R_3)]$ to the polymer backbone $[-(CH_2-CR_1)_n-]$.

$L_2$ is a linker that covalently couples the anionic center $[A(=O)-O^-]$ to the cationic center;

A is C, S, SO, P, or PO;

$M^+$ is a counter ion associated with the $(A=O)O^-$ anionic center;

$X^-$ is a counter ion associated with the cationic center; and n is an integer from 1 to about 10,000.

In one aspect, the invention provides a mixed charge copolymer conjugate, comprising a lipid covalently coupled to mixed charge copolymer.

In one embodiment, the mixed charge copolymer comprises a plurality of repeating units, each repeating unit having the formula:

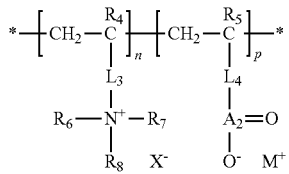

wherein $R_4$ and $R_5$ are independently selected from hydrogen, fluorine, trifluoromethyl, C1-C6 alkyl, and C6-C12 aryl groups;

$R_6$, $R_7$, and $R_8$ are independently selected from alkyl and aryl, or taken together with the nitrogen to which they are attached form a cationic center;

$A(=O)-OM)$ is an anionic center, wherein A is C, S, SO, P, or PO, and M is a metal or organic counterion;

$L_3$ is a linker that covalently couples the cationic center $[N^+(R_6)(R_7)(R_8)]$ to the polymer backbone;

$L_4$ is a linker that covalently couples the anionic center $[A(=O)-OM]$ to the polymer backbone;

$X^-$ is the counter ion associated with the cationic center;

n is an integer from 1 to about 10,000; and p is an integer from 1 to about 10,000.

For the above conjugates, in one embodiment, the lipid is a diacylphosphatidylethanolamine or a diacylphosphatidylglycerol. In one embodiment, the lipid is selected from the group consisting of dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, 1-stearoyl-2-oleoyl-phosphatidyethanolamine (SOPE), and 1,2-dioleoyl-sn-glycero-3-phophoethanolamine (transDOPE). In one embodiment, the lipid is distearoyl-phosphatidylethanolamine (DSPE).

In other aspects, the invention provides particles.

In one embodiment, the invention provides a core-shell polymeric particle, comprising a plurality of block copolymers of the invention.

In one embodiment, the invention provides a micelle, comprising a plurality of conjugates of liposome, comprising a plurality of conjugates of the invention.

In one embodiment, the invention provides a liposome, comprising a plurality of conjugates of the invention.

In one embodiment, the invention provides a polymersome, comprising a plurality of block copolymers of the invention.

The particles can further include one or more targeting agents, and one or more therapeutic and/or one or more diagnostic agents.

In other aspects, the invention provides compositions that include one or more of the particles of the invention and a pharmaceutically accepted carrier or diluent.

In further aspects, the invention provides methods for delivering a therapeutic and/or diagnostic agent, comprising administering a composition of the invention to a subject in need thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

(FIG. 8B). NP size (mean±SD, n=3) was plotted as a function of time.

DETAILED DESCRIPTION OF THE INVENTION

Figure 1:
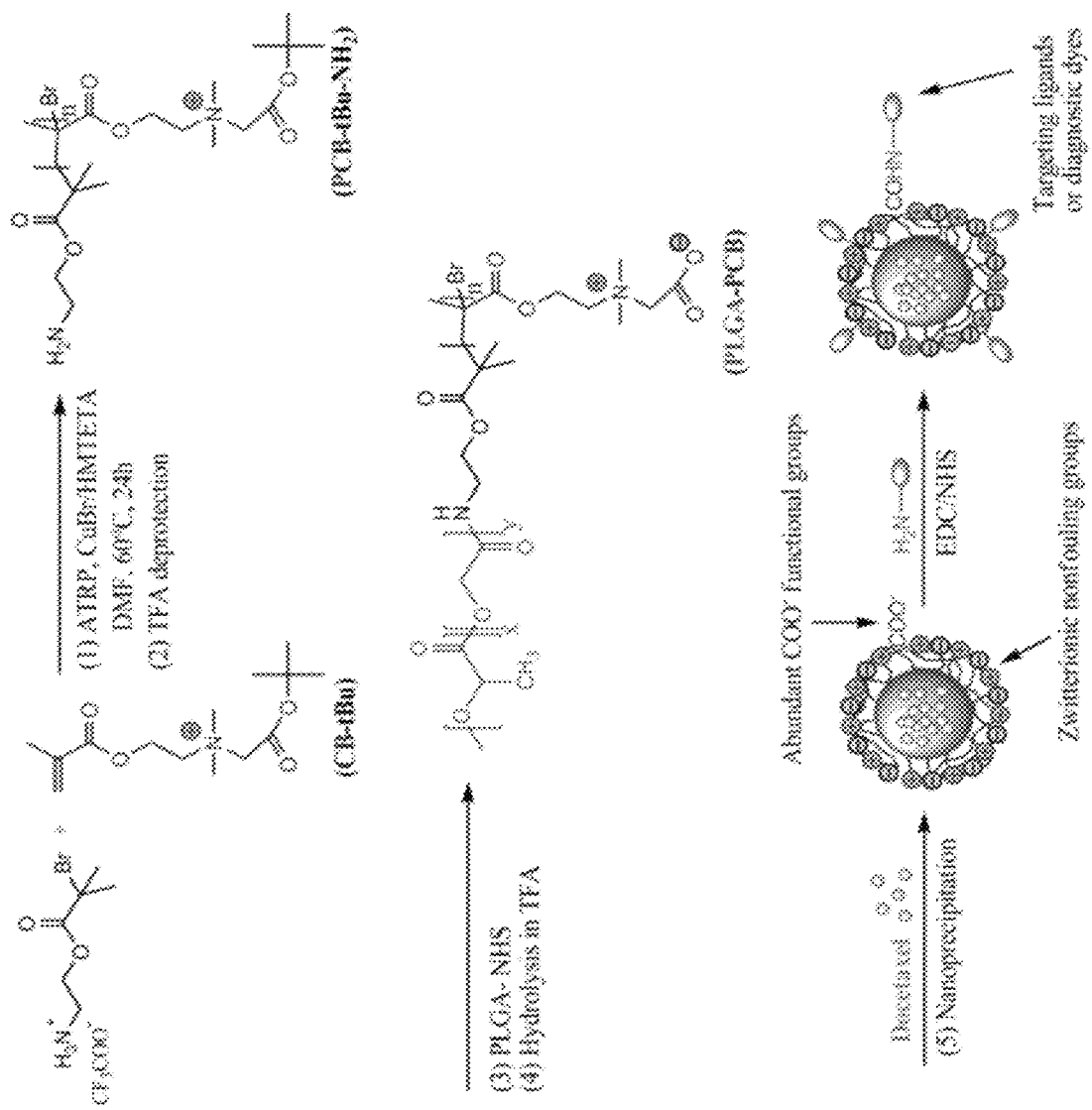
FIG. 1 is a schematic illustration of the preparation of a representative zwitterionic polymer conjugate of the invention, PLGA-PCB copolymers; formation of PLGA-PCB/Dtxl NPs; and post-functionalization of NPs with targeting ligands or diagnostic dyes.

The present invention provides block copolymers and conjugates that advantageously self-assemble into particles. The invention further includes particles assembled from the block copolymers and conjugates, pharmaceutical compositions that include the self-assembled particles, and methods for delivering therapeutic and diagnostic agents using the particles. Methods for making the block copolymers and conjugates and related particles are also provided.

Block Copolymers

In one aspect, the invention provides block copolymers. In one embodiment, the block copolymer is a zwitterionic block copolymer. In another embodiment, the block copolymer is a mixed charge block copolymer Zwitterionic Block Copolymer In one embodiment, the invention provides a zwitterionic block copolymer. As used herein, the term "zwitterionic block copolymer" refers to a block copolymer having a zwitterionic polymer block.

In one embodiment, the block copolymer is a zwitterionic block copolymer comprising:
(a) a zwitterionic block comprising a poly(carboxybetaine), a poly(sulfobetaine), or a poly(phosphobetaine); and
(b) a hydrophobic block.

In one embodiment, the zwitterionic polymer block comprises a plurality of repeating units, each repeating unit having the formula (I):

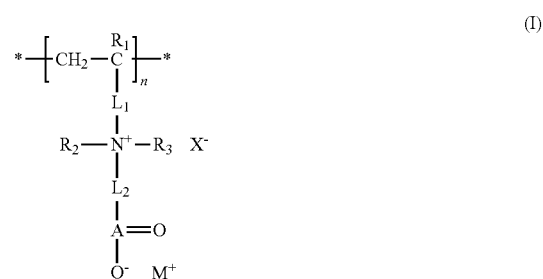

wherein
$R_1$ is selected from the group consisting of hydrogen, fluorine, trifluoromethyl, C1-C6 alkyl, and C6-C12 aryl groups;
$R_2$ and $R_3$ are independently selected from the group consisting of alkyl and aryl, or taken together with the nitrogen to which they are attached form a cationic center;
$L_1$ is a linker that covalently couples the cationic center $[N^+R_2)(R_3)]$ to the polymer backbone $[—(CH_2—CR_1)_n—]$.
$L_2$ is a linker that covalently couples the anionic center $[A(=O)—O^-]$ to the cationic center;
A is C, S, SO, P, or PO;
$M^+$ is a counter ion associated with the $(A=O)O^-$ anionic center;
$X^-$ is a counter ion associated with the cationic center;
n is an integer from 1 to about 10,000; and
* represents the point at which the repeating unit is covalently linked to the next.

Mixed Charge Block Copolymer

In one embodiment, the invention provides a mixed charge block copolymer. In one embodiment, the block copolymer is a mixed charge block copolymer comprising:
(a) a mixed charge copolymer block comprising a poly (carboxybetaine), a poly(sulfobetaine), or a poly(phosphobetaine); and
(b) a hydrophobic block.

As used herein, the term "mixed charge block copolymer" refers to a block copolymer having a mixed charge polymer block.

As used herein, the term "mixed charge copolymer" refers to a copolymer having a polymer backbone, a plurality of positively charged repeating units, and a plurality of negatively charged repeating units. In the practice of the invention, these copolymers may be prepared by polymerization of an ion-pair comonomer.

The mixed charge copolymer includes a plurality of positively charged repeating units, and a plurality of negatively charged repeating units. In one embodiment, the mixed charge copolymer is substantially electronically neutral. As used herein, the term "substantially electronically neutral" refers to a copolymer that imparts advantageous nonfouling properties to the copolymer. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

Ion Pair Comonomers. In one embodiment, the copolymers are prepared by copolymerization of suitable polymerizable ion pair comonomers.

Representative ion-pair comonomers useful in the invention have formulas (II) and (III):

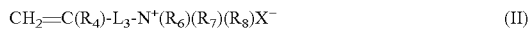
(II)

(III)

In this embodiment, the mixed charge copolymer has repeating units having formula (IV):

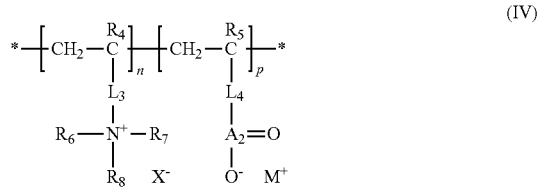
(IV)

wherein $R_4$ and $R_5$ are independently selected from hydrogen, fluorine, trifluoromethyl, C1-C6 alkyl, and C6-C12 aryl groups;

$R_6$, $R_7$, and $R_8$ are independently selected from alkyl and aryl, or taken together with the nitrogen to which they are attached form a cationic center;

A(=O)—OM) is an anionic center, wherein A is C, S, SO, P, or PO, and M is a metal or organic counterion;

$L_3$ is a linker that covalently couples the cationic center [$N^+(R_6)(R_7)(R_8)$] to the polymer backbone;

$L_4$ is a linker that covalently couples the anionic center [A(=O)—OM] to the polymer backbone;

$X^-$ is the counter ion associated with the cationic center;

n is an integer from 1 to about 10,000;

p is an integer from 1 to about 10,000; and

* represents the point at which the repeating units is covalently linked to the next.

In one embodiment, $R_7$ and $R_8$ are C1-C3 alkyl.

$R_6$, $R_7$, and $R_8$ are independently selected from alkyl and aryl, or taken together with the nitrogen to which they are attached form a cationic center. In one embodiment, $R_6$, $R_7$, and $R_8$ are C1-C3 alkyl.

In certain embodiments, $L_3$ is selected from the group consisting of —C(=O)O—$(CH_2)_n$— and —C(=O)NH—$(CH_2)_n$—, wherein n is an integer from 1 to 20. In certain embodiments, $L_3$ is —C(=O)O—$(CH_2)_n$—, wherein n is 1-6.

In certain embodiments, $L_4$ is a C1-C20 alkylene chain. Representative $L_4$ groups include —$(CH_2)_n$—, where n is 1-20 (e.g., 1, 3, or 5)

In certain embodiments, A is C or SO.

In certain embodiments, n is an integer from 5 to about 5,000.

In one embodiment, $R_4$, $R_5$, $R_6$, $R_7$, and $R_8$ are methyl, $L_3$ is —C(=O)O—$(CH_2)_2$—, and $L_4$ is —$CH_2$—, $A_1$ is C or SO, and n is an integer from 5 to about 5,000.

In the above formulas, the polymer backbones include vinyl backbones (i.e., —C(R')(R")—C(R''')(R'''')—, where R', R", R''', and R'''' are independently selected from hydrogen, alkyl, and aryl) derived from vinyl monomers (e.g., acrylate, methacrylate, acrylamide, methacrylamide, styrene).

In the above formulas, $N^+$ is the cationic center. In certain embodiments, the cationic center is a quaternary ammonium (e.g., N bonded to $L_1$, $R_2$, $R_3$, and $L_2$). In addition to ammonium, other useful cationic centers (e.g., $R_2$ and $R_3$ taken together with N) include imidazolium, triazaolium, pyridinium, morpholinium, oxazolidinium, pyrazinium, pyridazinium, pyrimidinium, piperazinium, and pyrrolidinium.

$R_1$-$R_8$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_2$ and $R_3$, and $R_6$, $R_7$, and $R_8$, are methyl. In one embodiment, $R_1$-$R_8$ are methyl. Representative aryl groups include C6-C12 aryl groups including, for example, phenyl. For certain embodiments of the above formulas, $R_2$ and $R_3$, and/or $R_6$, $R_7$, and $R_8$ are taken together with $N^+$ form the cationic center.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomers). In addition to the functional group, $L_1$ can include an C1-C20 alkylene chain. Representative $L_1$ groups include —C(=O)O—$(CH_2)_n$— and —C(=O)NH—$(CH_2)_n$—, where n is 1-20 (e.g., n=2).

$L_2$ is a linker that covalently couples the cationic center to the anionic group. $L_2$ can be a C1-C20 alkylene chain. Representative $L_2$ groups include —$(CH_2)_n$—, where n is 1-20 (e.g., 1, 3, or 5).

$L_3$ is a linker that covalently couples the cationic center to the polymer backbone. In certain embodiments, $L_3$ includes a functional group (e.g., ester or amide) that couples the remainder of $L_3$ to the polymer backbone (or polymerizable moiety for the monomers). In addition to the functional group, $L_3$ can include an C1-C20 alkylene chain. Representative $L_3$ groups include —C(=O)O—$(CH_2)_n$— and —C(=O)NH—$(CH_2)_n$—, where n is 1-20 (e.g., n=2).

$L_4$ is a linker that covalently couples the anionic group to the polymer backbone. $L_4$ can be a C1-C20 alkylene chain. Representative $L_4$ groups include —$(CH_2)_n$—, where n is 1-20 (e.g., 1, 3, or 5).

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl).

Representative aryl groups include C6-C12 aryl groups including, for example, phenyl including substituted phenyl groups (e.g., benzoic acid).

$X^-$ is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4^-$); tetrafluoroborate ($BF_4^-$); hexafluorophosphate ($PF_6^-$); trifluoromethylsulfonate ($SO_3CF_3^-$); and derivatives thereof. Other suitable counter ions include salicylic acid (2-hydroxybenzoic acid), benzoate, and lactate.

For the zwitterionic polymers and mixed charge copolymers useful in the invention, the degree of polymerization (DP or n), number average molecular weight ($M_n$), and the ratio of weight average and number average molecular weights ($M_w/M_n$), also known as polydispersity index, can vary. In one embodiment, the polymers have a degree of polymerization (n) from 1 to about 10,000. In one embodiment, n is from about 10 to about 5,000. In another embodiment, n is from about 100 to about 3,500. In one embodiment, the polymers have a number average molecular weight ($M_n$) of from about 200 to about 2,000,000 Da. In one embodiment, $M_n$ is from about 2,000 to about 100,000 Da. In another embodiment, $M_n$ is from about 20,000 to about 80,000 Da. In one embodiment, the polymers have a ratio of weight average and number average molecular weight ($M_w/M_n$) of from about 1.0 to about 2.0. In one embodiment, $M_w/M_n$ is from about 1.1 to about 1.5. In another embodiment, $M_w/M_n$ is from about 1.2 to about 2.0.

In the block copolymers, the hydrophobic block is the portion of the copolymer that forms the core of the core-shell particle. Suitable hydrophobic blocks comprise a polymeric block that is biocompatible polymer. The hydrophobic block can be comprised of a homopolymer or copolymer. The zwitterionic polymer block or the mixed charge copolymer block form the shells of the particle.

Representative biodegradable hydrophobic blocks include peptides, polyesters, polyorthoesters, polyanhydrides, polyesteramides, and polyoxaesters, and their derivatives or combinations thereof.

Representative hydrophobic blocks comprise a polymer selected from poly(lactic-co-glycolic acid) (PLGA), polycaprolactone (PCL), polyglycolide (PG), polylactic acid (PLA), poly-3-hydroxybutyrate, polydioxanone, polytrimethylenecarbonate, poly(glycolide-co-caprolactone) (Monocryl™), poly(glycolide-co-trimethylenecarbonate) (Maxon™), and poly(dioxanon-co-trimethylenecarbonate-co-glycolide) (BioSyn™).

In certain embodiments, the hydrophobic block has a number average molecular weight from about 1,000 to about 200,000 Da.

The block copolymers can be prepared by preparing a radical initiator based on the hydrophobic block (hydrophobic polymer functionalized to include a terminal radical initiator group) followed by polymerization of a suitable carboxybetaine monomer. Alternatively, the block copolymers can be prepared by covalently coupling a suitably functionalized hydrophobic polymer (e.g., end terminal amino group) to a suitably functionalized zwitterionic polymer (e.g., end terminal carboxy group or reactive derivative thereof) or their hydrophobic derivatives (e.g., cationic ester derivatives).

Conjugates

In another aspect, the invention provides conjugates. In one embodiment, the conjugate is a zwitterionic polymer conjugate. In another embodiment, the conjugate is a mixed charge copolymer conjugate. Like the block copolymers described above, the conjugates include a hydrophobic portion that comprises the core of the particle on self-assembly of the conjugate. The particle shell is comprised of the zwitterionic polymer portion or mixed charge copolymer portion.

Zwitterionic Conjugate

In one embodiment, the invention provides a zwitterionic polymer conjugate comprising a lipid covalently coupled to a poly(carboxybetaine), a poly(sulfobetaine) or a poly(phosphobetaine). In another embodiment, the invention provides a mixed charge copolymer conjugate comprising a lipid covalently coupled to a poly(carboxybetaine), a poly(sulfobetaine) or a poly(phosphobetaine).

Lipids suitable for use in the conjugates can be selected from a variety of synthetic vesicle-forming lipids or naturally-occurring vesicle-forming lipids. These lipids include phospholipids, sphingolipids, and sterols. The lipid contain a chemical group such as amine group, hydroxyl group, aldehyde group, or carboxylic acid group at its polar head group suitable for covalent attachment of the zwitterionic polymer or mixed charge copolymer chains.

One embodiment includes two hydrocarbon chains, such as phosphatidylethanolamine (PE), phosphatidylglycerol (PG), phosphatidic acid (PA), or phosphatidylinositol (PI), where each hydrocarbon chain contain 3-24 carbon atoms in length and have varying degrees of unsaturation.

Suitable lipids include those derived from diacylphosphatidylethanolamines, ceramides, sphingomyelins, dihydrosphingomyelins, cephalins, and cerebrosides. For the diacyl compounds, the acyl group is a fatty acid group (e.g., C8-C40).

In certain embodiments, the lipid is a diacylphosphatidylethanolamine or a diacylphosphatidylglycerol.

Representative lipids include dioleoylphosphatidylglycerol (DOPG), dipalmitoylphosphatidylglycerol (DPPG), dioleoyl-phosphatidylethanolamine (DOPE), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, 1-stearoyl-2-oleoyl-phosphatidyethanolamine (SOPE), and 1,2-dioleoyl-sn-glycero-3-phophoethanolamine (transDOPE).

In one embodiment, the hydrophobic moiety is distearoyl-phosphatidylethanolamine (DSPE).

For the zwitterionic polymer conjugates, the zwitterionic polymer portion of the conjugate is the same as described above for the zwitterionic polymer block (i.e., formula (I)).

For the mixed charge copolymer conjugates, the mixed charge copolymer portion of the conjugate is the same as described above for the mixed charge copolymer block (i.e., formula (IV)).

The conjugates can be prepared by covalently coupling a suitably functionalized hydrophobic moiety (e.g., end terminal amino) to a suitably functionalized zwitterionic polymer or mixed charge copolymer (e.g., end terminal carboxy group or reactive derivative thereof) or their hydrophobic derivatives (e.g., cationic ester derivatives).

The preparation and characteristics of representative zwitterionic conjugates of the invention, corresponding particles that include a therapeutic drug, and liposome formulations of the particles are described in Example 1.

Particles

In another aspect of the invention, particles formed from the zwitterionic block copolymers and zwitterionic conjugates are provided. Because of the nature of the copolymers and conjugates, the particles can be formed by self-assembly in aqueous environments. In an aqueous environment (e.g., physiological environment), the particles have a hydrophobic core comprising the hydrophobic portion of the copolymer, and a hydrophilic shell comprising the highly charged zwitterionic portion of the copolymer. In another embodiment, the particles have the form of a micelle composed of the conjugate.

In certain embodiments, the particles can have a vesicle structure. In one embodiment, the particles have the form of a liposome, formulated from the conjugate and other vesicle-forming lipids. These vesicle-forming lipids can be selected from a variety of synthetic vesicle-forming lipids or naturally-occurring vesicle-forming lipids. These lipids include phospholipids, sphingolipids, and sterols. In another embodiment, the particles have the form of a polymersome, formulated from the copolymers. For the delivery of cargo, such as therapeutic and/or diagnostic agents, core-shell nanoparticles and micelles are suitable to encapsulated hydrophobic cargo, and liposomes and polymersomes prefer hydrophilic cargo, although hydrophobic cargo can also be encapsulated.

In another embodiment, the invention provides a particle comprising a plurality of zwitterionic conjugates of the invention. In certain embodiments, the particles further include one or more vesicle-forming lipids.

In one embodiment, the particle is a core-shell nanoparticle.

In one embodiment, the particle is a polymersome.

In one embodiment, the particle is a micelle.

In one embodiment, the particle is a liposome.

Core-shell nanoparticles and micelles are useful to coat hydrophobic particles. Hydrophobic particles include metal particles (e.g., gold, silver, iron oxide, quantum dots) and polymeric particles.

In certain embodiments, the particles have a mean hydrodynamic diameter of from about 5 to about 5000 nm. In certain embodiments, the particles have a mean hydrodynamic diameter of from about 5 to about 500 nm. In other embodiments, the particles have a mean hydrodynamic diameter of from about 5 to about 200 nm. Rigid NPs with diameter larger than kidney glomerulus pore (about 5 nm) can effectively reduce renal filtration, thus increasing blood circulation time. Tumor vasculature has larger pore sizes than normal tissues (40-80 nm or even 1 µm), thus allowing passive leakage of suitable sized NPs into tumors, which is called the enhanced permeation and retention (EPR) effect.

Therapeutic Agents. In certain embodiments, the particles of the invention further include one or more therapeutic agent. Exemplary therapeutic agents that may be used in accordance with the present invention include small molecules, organometallic compounds, nucleic acids, proteins (including multimeric proteins, protein complexes, peptides), lipids, carbohydrates, hormones, metals, radioactive elements and compounds, drugs, vaccines, immunological agents, and/or combinations thereof.

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, antipyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A more complete listing of classes and specific drugs suitable for use in the present invention may be found in Pharmaceutical Drugs: Syntheses, Patents, Applications by Axel Kleemann and Jurgen Engel, Thieme Medical Publishing, 1999 and the Merck Index: An Encyclopedia of Chemicals, Drugs and Biologicals, Ed. by Budavari et al, CRC Press, 1996, both of which are incorporated herein by reference.

In certain embodiments of the invention, the therapeutic agent is a nucleic acid (e.g., DNA, RNA, derivatives thereof). In some embodiments, the nucleic acid agent is a functional RNA. In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g., short interfering RNAs (siRNAs), short hairpin RNAs (shRNAs), and microRNAs), ribozymes, tRNAs, rRNAs, RNAs useful for triple helix formation.

In some embodiments, the nucleic acid agent is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell. In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell. In some embodiments, a vector directs expression of any of the functional RNAs described herein, such as RNAi-inducing entities, ribozymes.

In some embodiments, the therapeutic agent may be a protein or peptide. The terms "protein," "polypeptide," and "peptide" can be used interchangeably. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size.

Polypeptides may contain L-amino acids, D-amino acids, or both and may contain any of a variety of amino acid modifications or analogs known in the art. Useful modifications include, e.g., terminal acetylation, amidation. In some embodiments, polypeptides may comprise natural amino acids, unnatural amino acids, synthetic amino acids, and combinations thereof, as described herein.

In some embodiments, the therapeutic agent may be a hormone, erythropoietin, insulin, cytokine, antigen for vaccination, growth factor. In some embodiments, the therapeutic agent may be an antibody and/or characteristic portion thereof. In some embodiments, antibodies may include, but are not limited to, polyclonal, monoclonal, chimeric (i.e., "humanized"), or single chain (recombinant) antibodies. In some embodiments, antibodies may have reduced effector functions and/or bispecific molecules. In some embodiments, antibodies may include Fab fragments and/or fragments produced by a Fab expression library (e.g. Fab, Fab', F(ab')2, scFv, Fv, dsFv diabody, and Fd fragments).

In some embodiments, the therapeutic agent is a carbohydrate. In certain embodiments, the carbohydrate is a carbohydrate that is associated with a protein (e.g., glycoprotein, proteogycan). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

In some embodiments, the therapeutic agent is a lipid. In certain embodiments, the lipid is a lipid that is associated with a protein (e.g., lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g., vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., C8-C50), substituted or unsubstituted hydrocarbons. In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Diagnostic Agents. In certain embodiments, the particles of the invention further include one or more diagnostic agents. In some embodiments, diagnostic agents include commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, a diagnostic and/or therapeutic agent may be a radionuclide. Among the radionuclides used, gamma-emitters, positron-emitters, and X-ray emitters are suitable for diagnostic and/or therapeutic purposes, while beta emitters and alpha-emitters may also be used for therapy. Suitable radionuclides for use in the invention include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211At, 212Bi, 212Pb, 109Pd, 111In, 67Ga, 68Ga, 67Cu, 75Br, 77Br, 99 mTc, 14C, 13N, 15O, 32P, 33P, and 18F.

In some embodiments, a diagnostic agent may be a fluorescent, luminescent, or magnetic moiety. Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook—A Guide to Fluorescent Probes and Labeling Technologies, Invitrogen, 10th edition, available at the Invitrogen web site).

In some embodiments, a diagnostic agent may be nanoparticles that can be detected by certain diagnostic methods, such as quantum dots, iron oxide, gold nanoparticles, nano-rod or nano-shell, carbon nanotube, nano-sheet, silica protected nanoparticles or combinations of these nano-materials.

In certain embodiments, the particles of the invention further include one or more therapeutic agent and/or one or more diagnostic agents.

Targeting Agents. In certain embodiments, the particles (either with or without cargo) further include one or more targeting agents.

Particles useful for therapeutic and diagnostic purposes can be advantageously treated with the polymers of the invention. In certain embodiments, the surface further comprises a plurality of target binding partners covalently coupled to a portion of the plurality of polymers adhered to the surface. In this embodiment, the target binding partner has affinity toward a target molecule. In these embodiments, the surfaces can be used in diagnostic assays.

The binding affinity of a target molecule toward to the surface results from the target binding partners immobilized on the surface. The target binding partner and the target molecule, each termed a binding pair member, form a binding pair. Each binding pair member is a molecule that specifically binds the other member. In one embodiment, the target binding partner has affinity to a target molecule with $K_d$ less than about $10^{-8}$.

A binding pair member can be any suitable molecule including, without limitation, proteins, peptides, proteins, poly- or oligo-saccharides, glycoproteins, lipids and lipoproteins, and nucleic acids, as well as synthetic organic or inorganic molecules having a defined bioactivity, such as an antibiotic, anti-inflammatory agent, or a cell adhesion mediator.

Examples of proteins that can be immobilized on the surfaces of the present invention include ligand-binding proteins, lectins, hormones, receptors, and enzymes. Representative proteins include antibodies (monoclonal, polyclonal, chimeric, single-chain or other recombinant forms), their protein/peptide antigens, protein-peptide hormones, streptavidin, avidin, protein A, proteins G, growth factors and their respective receptors, DNA-binding proteins, cell membrane receptors, endosomal membrane receptors, nuclear membrane receptors, neuron receptors, visual receptors, and muscle cell receptors. Representative oligonucleotides that can be immobilized on the surfaces of the present invention include DNA (genomic or cDNA), RNA, antisense, ribozymes, and external guide sequences for RNase P, and can range in size from short oligonucleotide primers up to entire genes.

Other target binding partners that bind specifically to a target compound include poly- or oligosaccharides on glycoproteins that bind to receptors, for example, the carbohydrate on the ligand for the inflammatory mediators P-selectin and E-selectin, and nucleic acid sequences that bind to complementary sequences, such as ribozymes, antisense, external guide sequences for RNase P, and aptamers.

In one embodiment, the target binding partner is an antibody, and the target molecule is an antigen against the antibody. In this embodiment, the surface of the invention specifically binds to the antigen and resists non-specific protein adsorption. In one embodiment, the target binding partner is a protein capable of promoting cell adhesion, and the target molecule is a cell. In this embodiment, the surface of the invention specifically binds to the cell and resists non-specific protein adsorption and non-specific cell adhesion.

The use of carboxybetaine polymer surfaces for immobilizing target binding partners is described in WO 2008/083390, expressly incorporated herein by reference in its entirety.

Pharmaceutical Compositions

In other aspects, the invention provides compositions that include the zwitterionic block copolymers and zwitterionic conjugates. In certain embodiments, the compositions are pharmaceutical compositions suitable for administration to subjects. These compositions include pharmaceutically accepted carriers or diluents.

Methods for Delivery of Therapeutic/Diagnostic Agents

In another aspect, the invention provides methods for using the particles.

In one embodiment, the invention provides methods for delivering a therapeutic and/or diagnostic agent to a subject in need of therapy or diagnosis. In the method, a composition comprising particles of one or more of the zwitterionic block copolymers and zwitterionic conjugates of the invention are administered to the subject.

The following is a description of representative zwitterionic block copolymers and zwitterionic conjugates, their particles, and the characteristics thereof.

In one embodiment, the present invention provides a zwitterionic material, poly(carboxybetaine) (PCB) that is unique in that each CB side chain has one carboxylate anion group for conjugation with amine-containing biomolecules while at the same time each carboxylate anion group is paired with one cationic quaternary amine group as a zwitterionic group to effectively resist non-specific protein adsorption even from complex media. The conjugation with biomolecules can be easily achieved via 1-ethyl-3-(3-dimethylaminopropyl)carbodiimide and N-hydroxysuccinimide (EDC/NHS) chemistry. After conjugation, unreacted NHS ester groups are hydrolyzed to carboxylate anions, which are paired with cationic quaternary amines to form nonfouling zwitterionic structures. However, for functionalizable COOH-terminated PEG, unreacted functional groups (e.g., carboxylate acid) can cause severe fouling problems, particularly in complex media. Thus, PCB has abundant functional groups and an ultra low fouling background all in one material, which does not compromise the two quite different properties: nonfouling and functionalization. When antibodies are immobilized on a PCB-coated sensor chips, the post-functionalized surface still maintains ultra-low fouling properties (e.g., <0.3 ng/cm$^2$ adsorbed protein even from undiluted blood plasma and serum) and biomarkers in blood can be detected with high sensitivity. Introduction of CB onto NP surfaces improves both stability and multi-functional abilities of drug delivery carriers.

In one aspect, the present invention provides a poly(lactic-co-glycolic acid) (PLGA)-based drug delivery system. PLGA, approved by the FDA, has been used to encapsulate and control drug release due to its hydrophobic and slow-hydrolysis nature in aqueous medium. In one embodiment, the invention provides zwitterionic block copolymers (e.g., PLGA-PCB block copolymers) that self-assemble into PLGA-core NPs with a PCB-shell for drug delivery.

PLGA-PCB NPs exhibit stabilizing effects due to the strong hydration of zwitterionic CB and the sharp hydrophilicity/hydrophobicity difference between the PLGA-core and the PCB-shell. This difference between two blocks is so great that no common solvents or mixed solvents can co-dissolve PLGA and PCB homopolymers. Thus, the synthesis of PLGA-PCB block copolymers is very challenging due to the solvent problem. To solve this issue, a new carboxybetaine tert-butyl (CB-tBu) ester monomer was prepared (see FIG. 1). Unlike zwitterionic CB, CB-tBu is a cationic ester monomer with solubility in organic solvents, thus enabling the covalent binding of PLGA with PCB-tBu polymers in a common solvent, such as acetonitrile. Zwitterionic CB structures can be regenerated by hydrolysis of the tBu ester groups in an acid environment, such as trifluoroacetic acid (TFA), after covalent bonding with PLGA. This synthetic route potentially broadens the applicability of zwitterionic CB molecules in organic synthesis, making reactions between polar zwitterionic CB and a wide range of hydrophobic molecules possible.

PLGA-PCB block copolymers may be prepared either via PLGA (with appropriate terminal group) initiated radical polymerization of CB or via conjugation of PLGA and PCB (e.g., COOH terminated-PLGA couples with NH$_2$ terminated-PCB). The latter route is preferred because the NH$_2$-PCB products can be conjugated to a wide range of COOH-terminated molecules, including the commercially available PLGA, potential chemo-drugs, and proteins or enzymes for stabilization and multifunctional purposes. However, direct conjugation of NH$_2$-PCB to COOH-PLGA blocks is difficult due to their dramatic difference in polarity of the two blocks. Zwitterionic PCB can only be dissolved in water or methanol, while PLGA cannot be dissolved in either solvent. PLGA is also known to be hydrolyzed by trace amounts of water. To solve these "solvent" problems, the invention provides a CB-tBu ester monomer (FIG. 1), which is stable and has solubility in anhydrous organic solvents such as acetonitrile and DMF. CB-tBu ester monomers are polymerized via an atom transfer radical polymerization (ATRP) method initiated by a TFA$^-$ NH$_3^+$-bearing initiator (2-aminoethyl 2-bromoisobutyrate) (FIG. 1, Step 1). After removal of the TFA salt, PCB-tBu-NH$_2$ with good solubility in organic solvents is obtained (FIG. 1, Step 2) enabling conjugation with PLGA-NHS in anhydrous acetonitrile to form PLGA-PCB-tBu block copolymers (FIG. 1, Step 3). The uniqueness of the tBu ester lies in the easy removal of the ester group by TFA to generate a zwitterionic CB structure while PLGA remains intact in such acidic environment (FIG. 1, Step 4). A 1-hour TFA treatment is sufficient to fully convert PCB-tBu to PCB without breaking the ester bond in its methylacrylate moiety, while up to 6 hours of TFA incubation will not destroy the ester backbone of PLGA. The resistance of PLGA and polylactic acid (PLA) to acid degradation is known. Thus, PCB-tBu can be used in a generic way for the synthesis of any amphiphilic block polymers containing one PCB block and another hydrophobic block, even though the hydrophobic part is subject to hydrolysis (e.g., PLA-PCB or PLGA-PCB).

Figure 2A:
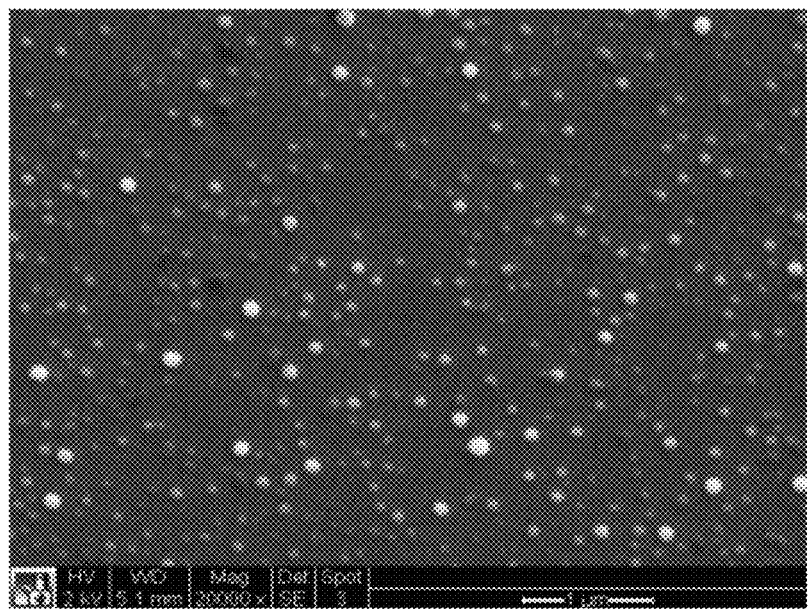
FIGS. 2A-2F illustrate the characteristics of representative zwitterionic polymer conjugate nanoparticles. Scanning electron microscopy (SEM) images for PLGA-PCB NPs before (FIG. 2A) and after (FIG. 2B) lyophilization and brief resuspension in water by pipettes without sonication. The scale bar is 1 μm. PLGA-PCB NP stability in PBS solutions of 10 wt % BSA and in 100% FBS at 37° C. over 5 days (FIG. 2C). NP size (Mean±SD, n=3) is plotted as a function of time. NP stability upon high-speed centrifugation for PLGA-PCB NPs (FIG. 2D) and PLGA-PCB/Dtxl NPs (1 wt % drug loading) (FIG. 2E) was tested with three successive centrifugation cycles. After each step of centrifugation (16110 g, 15 min), supernatants were either removed or kept and the NP pellets were re-suspended by pipettes without sonication. Stability of PLGA NPs, PLGA-PCB NPs, and PLGA-PCB/Dtxl NPs with 1 wt % drug loading after lyophilization without any addition of a cryoprotectant (FIG. 2F). NP size (Mean±SD, n=3) is plotted and the polydispersity indexes (PDIs, Mean±SD, n=3) accompanying each size point are indicated.

To formulate PLGA-PCB NPs, a solvent displacement method (or nanoprecipitation method) was used in which the block copolymer is dissolved in a water-miscible organic solvent. Upon addition of water, in which the PCB block is soluble but PLGA block is not, "PLGA core-PCB shell" structured NPs form. The organic solvent is evaporated while stirring, leaving an aqueous solution in which NPs harden. When hydrophobic drugs are mixed with copolymers in the organic solvent, they become encapsulated in the hydrophobic core of the NP during the process described above (FIG. 1, Step 5). An organic solvent can play a decisive role in NP formation due to the sharp difference in polarity between PLGA and PCB blocks. A single solvent, such as 2,2,2-trifluoroethanol (TFE), can dissolve PLGA-PCB largely due to the solubility of PLGA in this solvent, but produces large particles with heterogeneous size distributions (515.8±50.0 nm, PDI=0.527±0.056). This results from the microscopic insoluble state of PCB blocks in TFE. Thus, the formation of inverted "PCB core-PLGA shell" micelles does not favor small and homogeneous NPs. To improve the solubility of PCB block in TFE, a TFE/MeOH co-solvent was used instead, and NPs with a monodisperse size distribution, e.g., NP size=148.8±1.1 nm; PDI=0.040±0.011 (FIG. 2A), were then fabricated in a reproducible way. Note that TFE is preferred over DMSO due to the easy evaporation of TFE upon stirring. For a typical formulation, PLGA-PCB copolymers self-assembled into NPs with very low PDI. The yield was nearly 100%, with no precipitates or micro-size particles formed via the assembly process. Thus, there was no need to use filtration to remove large particles. No surfactant is required during solvent displacement since zwitterionic PCB shells stabilize the NPs in aqueous medium. Compared with PEGylated NP systems, PCB has better stabilization effect on NP dispersion because PCB is far more hydrophilic than PEG, thus less chain embedment by PLGA is expected during the self-assembly process. The sharp polarity difference between the copolymer blocks is responsible for such efficient assembly into small and homogeneous NPs. The zeta-potential for PLGA-PCB NPs obtained above was measured to be −43.5±1.0 mV, while PLGA NPs with the same size (NP size=145.7±3.9 nm; PDI=0.113±0.033) had a zeta-potential of −68.1±1.8 mV.

Docetaxel was encapsulated into the PLGA-PCB NPs via the method above, and the drug release profile was collected. For an initial drug input of 5 wt % in the formulation, the resulting PLGA-PCB/Dtxl NPs had about 1 wt % (0.933±0.021 wt %) drug load, a size of 138.5±0.6 nm, PDI of 0.125±0.017, and zeta potential of −34.8±1.3 mV. PCB-modified and unmodified-PLGA NPs have similar sustained drug releasing profiles over 96 hours with 50% of the encapsulated drug released in the first 8 hours. Drug release kinetics can be further tuned by changing the length of the PLGA blocks; the rate of drug releasing can be prolonged by increasing the molecular weight of PLGA.

Figure 2B:
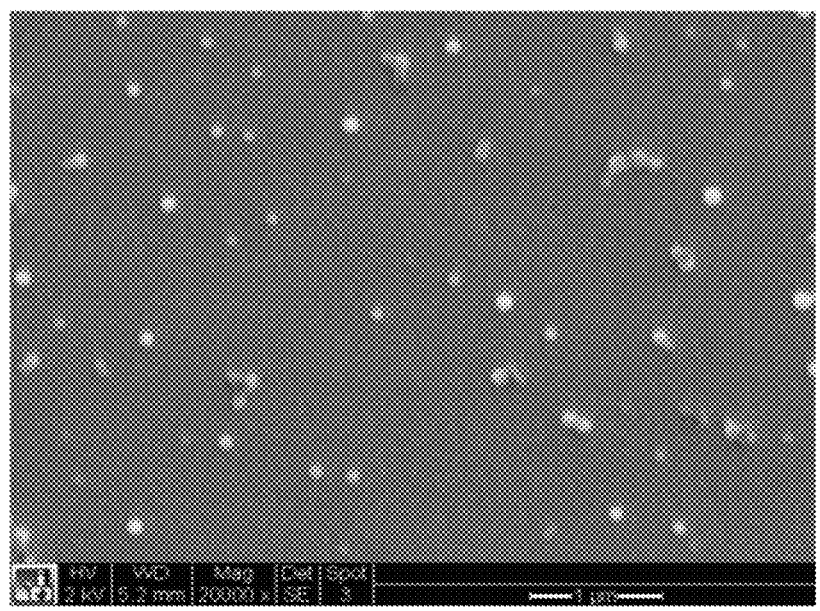
Figure 2C:
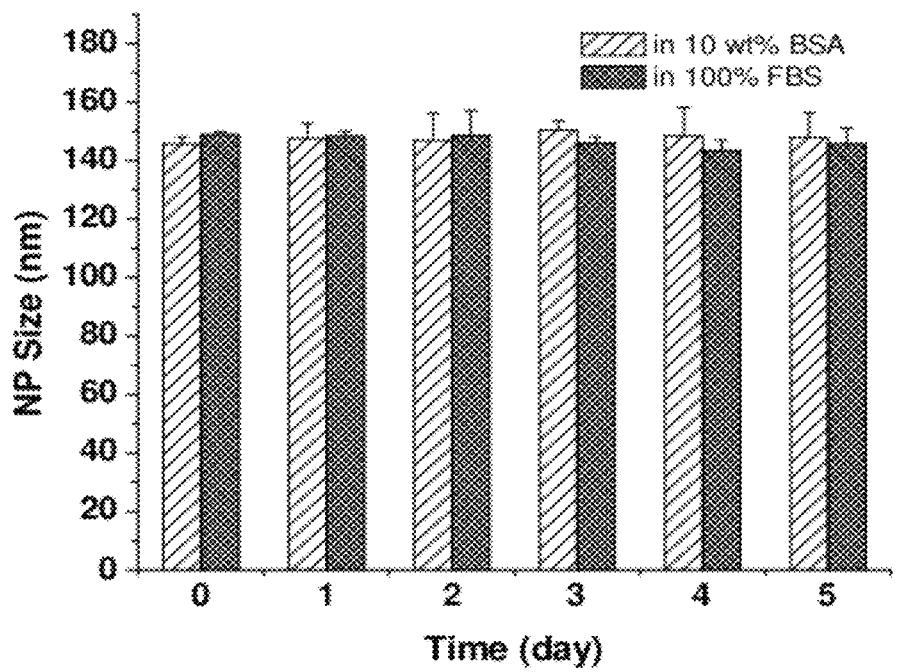

The stability of NPs in biologically relevant media such as serum determines their feasibility as drug delivery vehicles for in vivo use. PCB, which has been found to effectively reduce non-specific protein binding on surfaces from undiluted blood plasma and serum, can stabilize hydrophobic PLGA NPs in complex media. PLGA-PCB NPs were placed in PBS solution of 10 wt % bovine serum albumin (BSA) or 100% FBS solution at 37° C. and the NP size was measured as a function of time. No size increase of PCB-modified NPs was observed during the 13-hour study, while unmodified PLGA NPs severely aggregated immediately after their immersion in these media. A long-term study of PLGA-PCB NPs shows that these particles maintain their original size over a 5-day period in both 10 wt % BSA and 100% FBS media (FIG. 2C). This implies that PLGA-PCB NPs can be used for in vivo drug delivery.

Figure 2D:
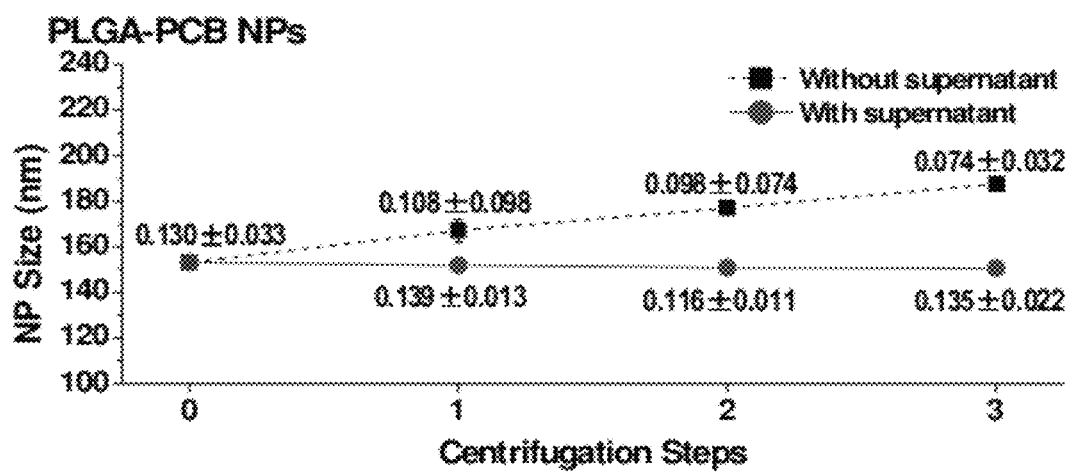
Figure 2E:
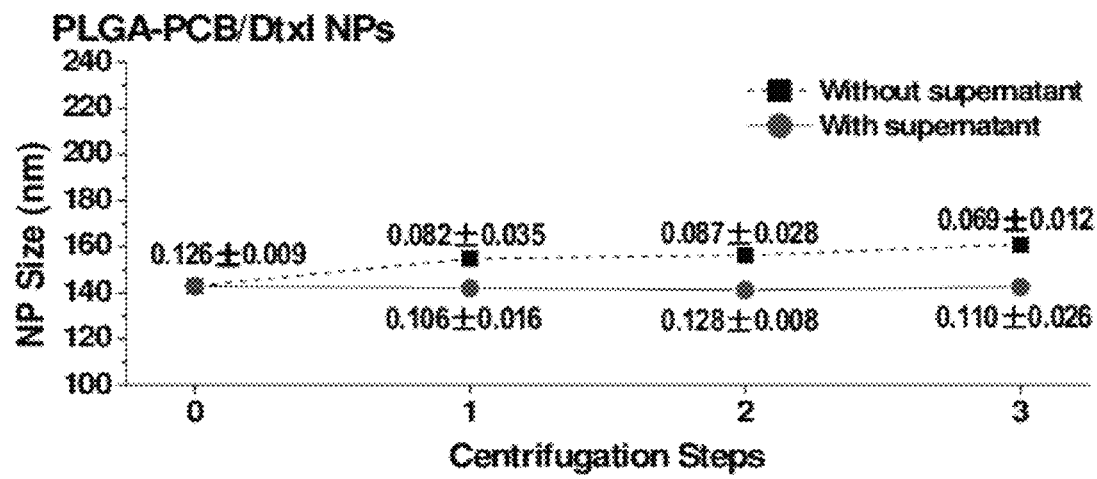

NP stability upon post-formulation or processing is also important from NPs created in a laboratory to their clinical use. Because PCB binds water through electrostatically induced hydration, it has stronger hydration than hydrogen-bonding materials such as PEG. It is expected that zwitterionic PCB polymers protect NPs from the harsh conditions of various steps of processing. High-speed centrifugation is widely used to form NP pellets for purification purposes, but PLGA-based NPs, including PEGylated NPs, tend to aggregate during pellet formation. PCB-modified PLGA NPs with or without drugs loaded were easily recovered from repeated high-speed centrifugation by brief pipette re-suspension of the pellets, thus abrogating the need for sonication. Pellets of unmodified PLGA NPs, once formed, however, cannot be resuspended without sonication. Specifically for PCB-modified NPs, when supernatants were removed at each centrifugation step (as in standard NP purification procedures), 6-9% and 1-8% increases in sizes were observed for PLGA-PCB NPs and PLGA-PCB/Dtxl NPs calculated from FIGS. 2D and 2E, respectively, with a slight decrease in PDI. The smaller PDIs obtained after each cycle do reflect the monodispersity of those remaining NPs. Note that there is a slight size increase after each cycle which is not caused by NP aggregation. Smaller NPs are less likely to form the pellet at each centrifugation step, and thus the removal of supernatants will shift the size distribution of the recovered portion towards larger values. To double confirm this stability issue, parallel experiments were performed in which the supernatant was not removed between centrifugation steps. It was found that NPs maintained the same size and PDI upon repeated centrifugation, indicating the ability of PCB to stabilize PLGA NPs (either with drug encapsulated or not) from any aggregation upon pelleting. This is due to the strong hydration layer created by the PCB shells of the NPs, stabilizing the hydrophobic PLGA cores from mechanically-induced aggregation.

Figure 2F:
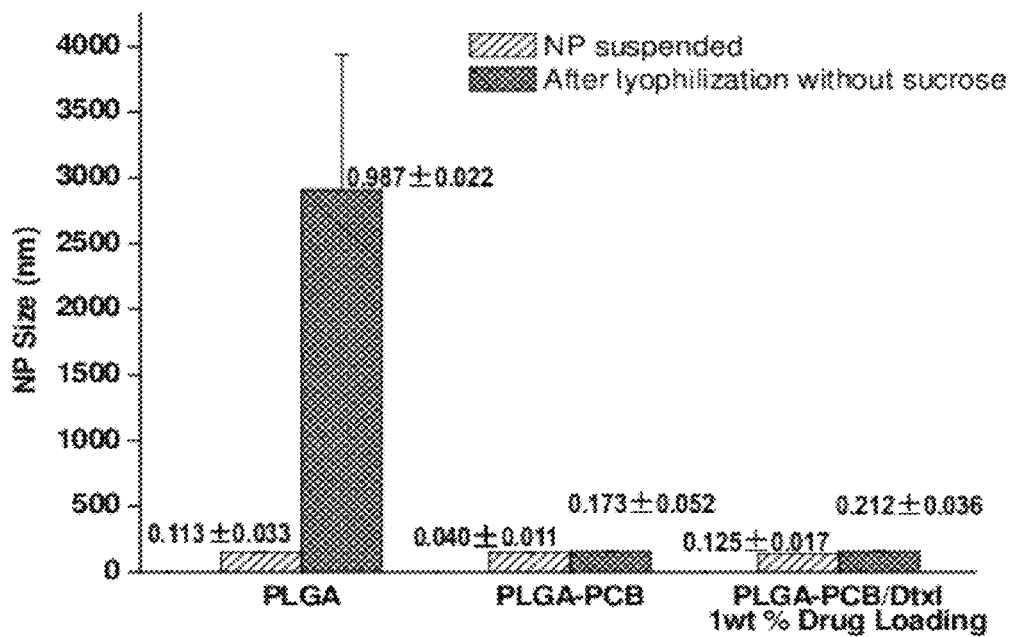

Freeze-drying is a necessary procedure for NP storage to prevent polymer degradation and drug leakage in aqueous storing media. No other polymer-based NPs can survive lyophilization without cryoprotectant additives. Even for PEGylated NPs, additives such as 10% sucrose are required, because PEG is crystallized upon freeze-drying and loses its function to prevent NP aggregation. The PCB-modified PLGA NPs retain their stability after freeze-drying without any additives (FIG. 2F). A brief re-suspension with pipettes (no sonication needed) of the dry PCB-modified NPs either with or without drug loaded recovers the NPs to the same mean diameter and low PDIs. These NPs were also visualized after freeze-drying by SEM (FIG. 2B). This behavior may result from strong PCB hydration and distinct PLGA/PCB blocks. Unlike PEG, PCB strongly binds a certain amount of water molecules to prevent crystallization during lyophilization. In addition, the efficient assembly of the copolymers due to the sharp polarity contrast between two blocks renders an almost defect-free protecting PCB shells keeping the hydrophobic cores apart even in a highly dehydrated environment. Due to their ability to survive in complex biological media and harsh post-formulation processing, zwitterionic PCB-modified NPs uniquely address both industrial and clinical stability concerns.

Figure 3A:
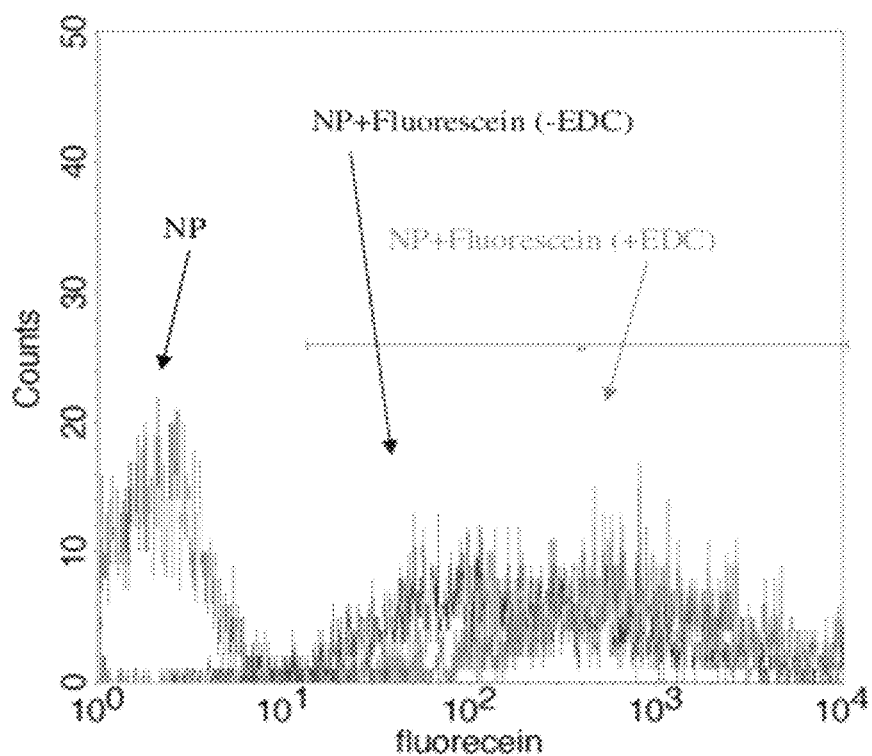
FIG. 3A illustrates the results of a studies on PLGA-PCB NPs conjugated with $NH_2$-Fluorescein. Bare NPs without fluorescein treatment, NPs treated with fluorescein (–EDC, +NHS), and NPs treated with fluorescein (+EDC, +NHS) are shown in black, blue, and green curves, respectively. NPs covalently bound with fluorescein (green lines) show a huge increase of mean fluorescence intensity over NPs (–EDC+ NHS+fluorescein). Binding of PLGA-PCB/NBD NPs functionalized with galactose to HepG2 cells. Cells were incubated for 2 h with PLGA-PCB/NBD NPs treated with $NH_2$-galactose (+EDC, +NHS) (FIG. 3B), and $NH_2$-galactose (–EDC, +NHS) (FIG. 3C). Fluorescence image and phase contrast image were taken at 20 h and combined as illustrated in the figure.
Figure 3B:
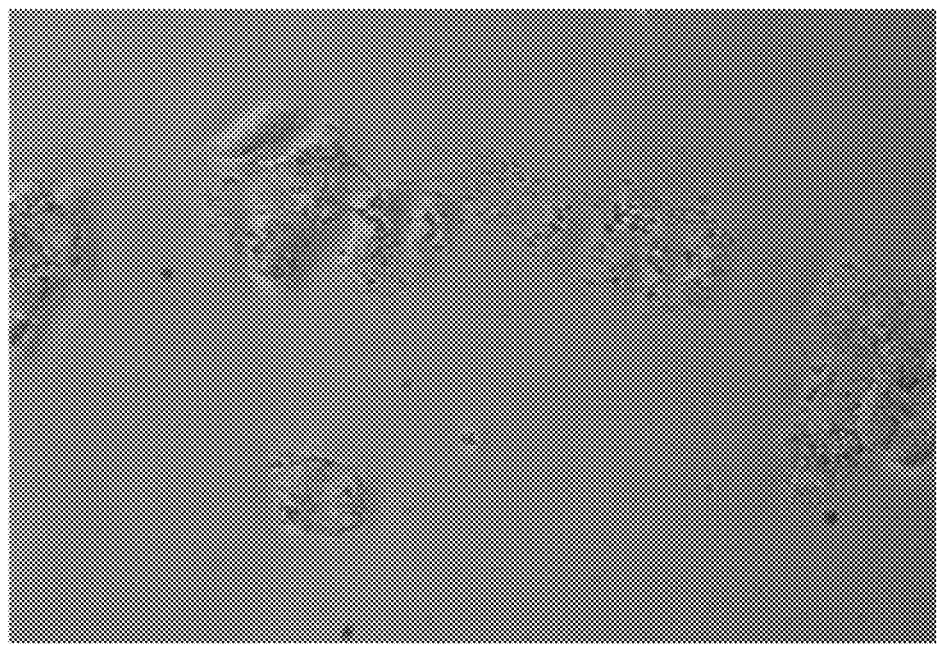
Figure 3C:
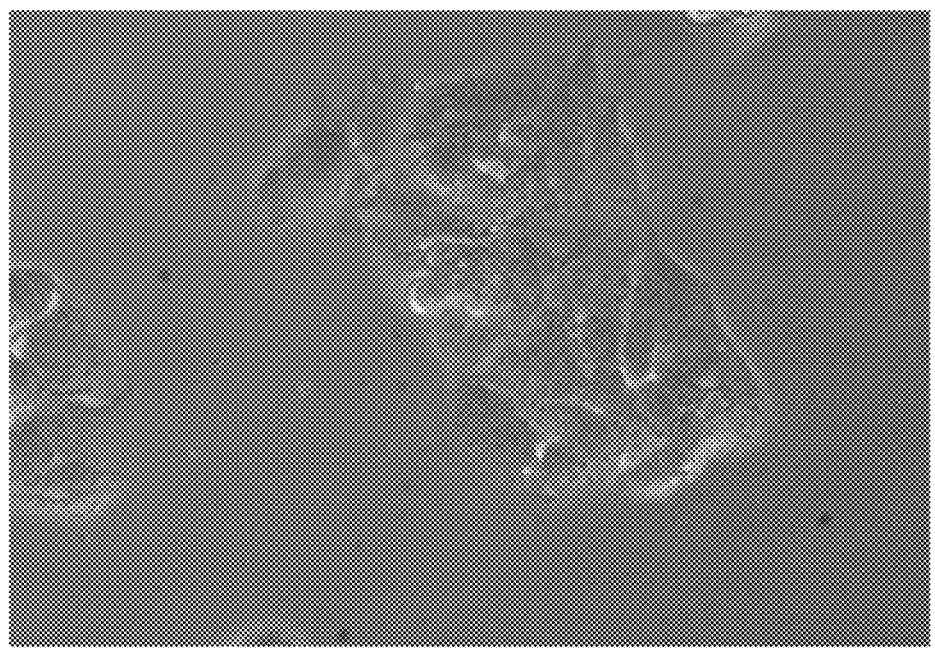

Functionalization of NPs is required to attach biomolecules such as dyes and targeting ligands for different purposes. To examine the feasibility of immobilizing those molecules of interest on PCB shells, fluorescein was used as a model ligand to generate fluorescent NPs. The carboxylate groups of PCB was converted to NHS ester in the presence of (+) EDC and NHS and later conjugated with amine groups in the fluorescein molecules. To confirm the conjugation chemistry on NP surfaces, NPs were prepared without generating NHS esters in the absence of (−) EDC but +NHS as the negative control. Any binding of the dyes onto NPs in the negative control should be due to physical interactions. After fluorescein incubation, NPs with NHS esters on the surfaces had significantly higher fluorescence intensity than controls due to their covalent coupling with the dyes (FIG. 3A). The potential of PLGA-PCB NPs as targeting drug delivery vehicles is also evaluated. A green fluorescent dye (NBD) was used as a "visible" model drug and encapsulated in the NPs. The resulting PLGA-PCB/NBD NPs were further conjugated with amine-modified galactose ligands with either +EDC and +NHS, or −EDC and +NHS, and then were incubated with HepG2 cells to test cell binding abilities. Galactose is widely used to target asialoglycoprotein receptors in hepatoma cell lines (e.g., HepG2) in vitro and hepatocytes in vivo. PLGA-PCB/NBD NPs with immobilized galactose ligands (+EDC, +NHS) readily bound to the cells, thus producing strong fluorescence as shown in FIG. 3B. PLGA-PCB/NBD NPs without the immobilized ligands (−EDC, +NHS) resulted in non-targeting and nonfouling NPs and thus had low cell binding abilities (FIG. 3C). These fluorescein and galactose/NBD results show that PCB-modified NPs can be easily functionalized with amine terminating molecules for imaging and/or targeting purposes.

The structure of CB is similar to that of glycine betaine, a solute which is vital to osmotic regulation of living organisms. Estimates of glycine betaine intake by humans are from 0.1 to 2.5 g/day. Thus modification of PLGA NPs with biomimetic PCB should not bring any toxicity to FDA-approved PLGA. Indeed, a cytotoxicity assay showed that PLGA-PCB NPs were similar to PLGA NPs in terms of the viability of HepG2 cells after 24 h incubation at NP concentrations up to 10 mg/ml. This concentration corresponds to over 500 mg/kg body weight for an adult human, which is a much higher dose required for in vivo drug delivery.

Figure 7:
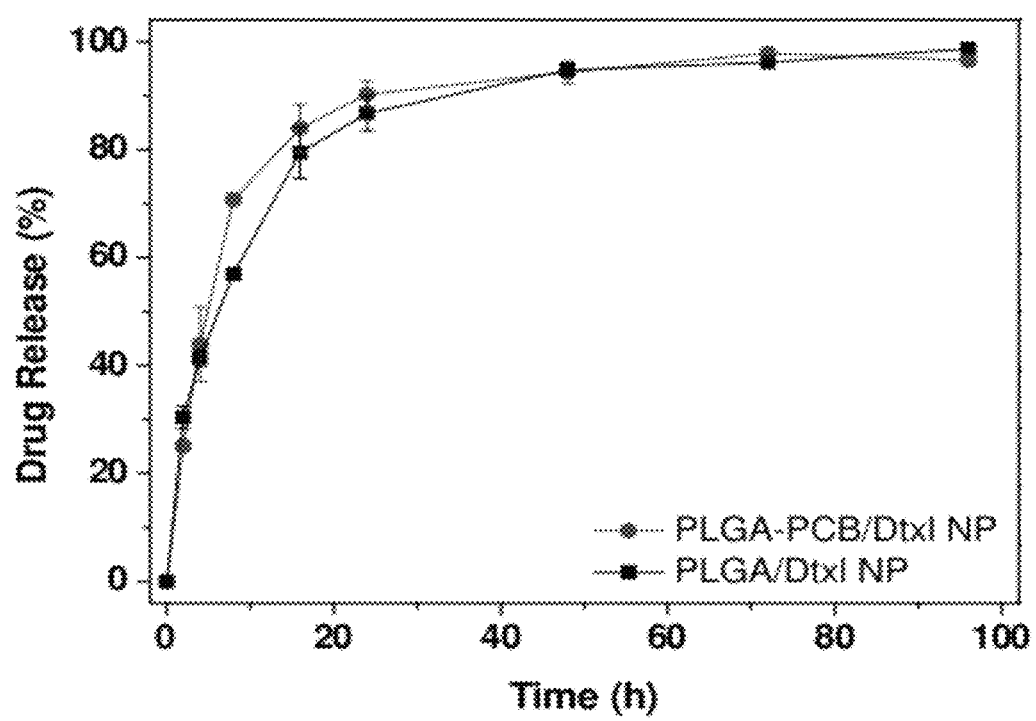
FIG. 7 compares docetaxel release profiles from representative nanoparticles of the invention, PLGA-PCB NPs, with PLGA NPs. Drug loading for both NPs was 1 wt %.
Figure 8A:
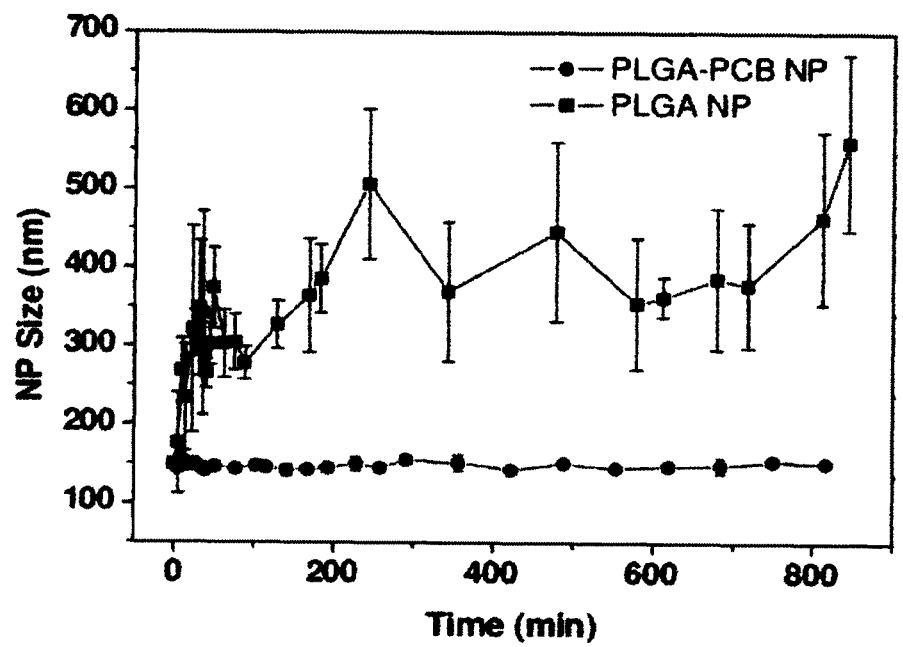
FIGS. 8A and 8B compare NP stability (nanoparticle size) in 10 wt % BSA solution in PBS (FIG. 8A), and 100% FBS solution at 37° C.
Figure 8B:
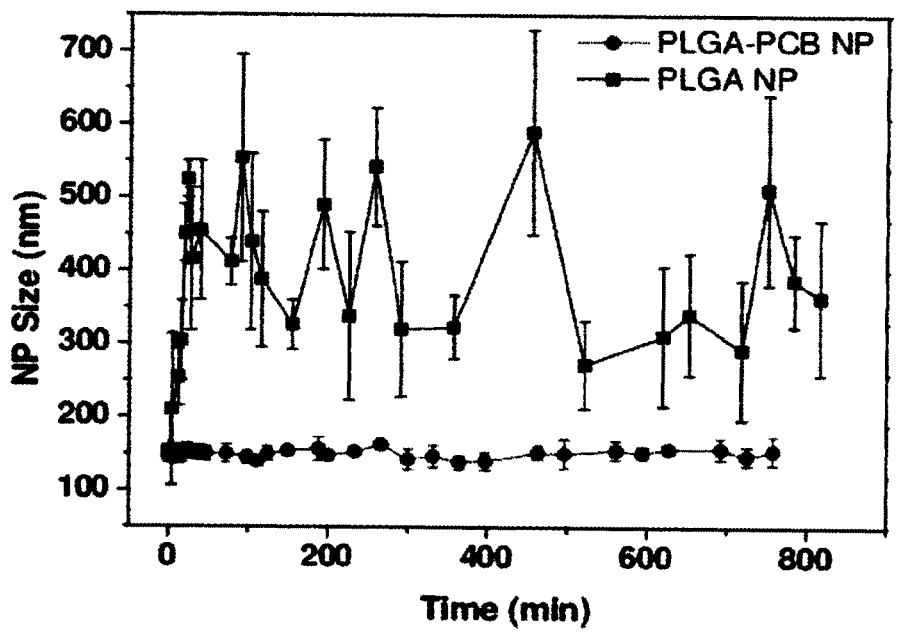
Figure 9:
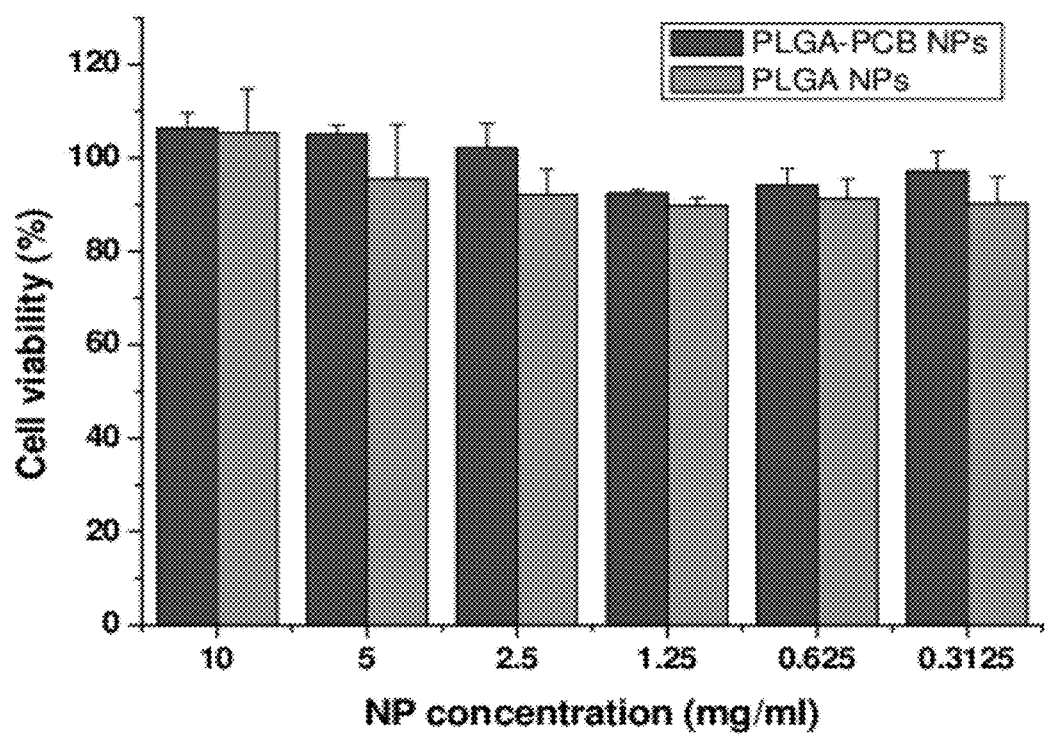
FIG. 9 compares cell viability (cytotoxicity) of representative nanoparticles of the invention, PLGA-PCB NPs, with PLGA NPs on HepG2 cells. NPs are incubated with the cells at indicated concentrations for 24 h, and immediately assayed for cell viability in triplicate.

The preparation and characteristics of a representative nanoparticle drug delivery system of the invention are described in Example 2. FIG. 7 compares docetaxel release profiles from representative nanoparticles of the invention, PLGA-PCB NPs, with PLGA NPs. Drug loading for both NPs was 1 wt %. PCB modification did not change drug releasing behavior much over unmodified PLGA. FIGS. 8A and 8B compare NP stability (nanoparticle size) in 10 wt % BSA solution in PBS (FIG. 8A), and 100% FBS solution at 37° C. (FIG. 8B). NP size (mean±SD, n=3) was plotted as a function of time. FIG. 9 compares cell viability (cytotoxicity) of representative nanoparticles of the invention, PLGA-PCB NPs, with PLGA NPs on HepG2 cells. NPs are incubated with the cells at indicated concentrations for 24 h, and immediately assayed for cell viability in triplicate. Similar to PLGA NPs, PLGA-PCB NPs exhibit no cytotoxicity at concentrations up to 10 mg/ml.

PCB-modified NPs are superior over PEGylated NPs for their easy processing, extraordinary stability, and non-compromised multi-functionality. The abundant carboxylate anion groups of PCB enable the attachment of targeting ligands, therapeutic drugs, and diagnostic labels all in one material through conventional NHS/EDC chemistry, making PCB a universal platform for "theranostics".

The following example are provided for the purpose of illustrating, not limiting, the invention.

EXAMPLE 1

Figure 4:
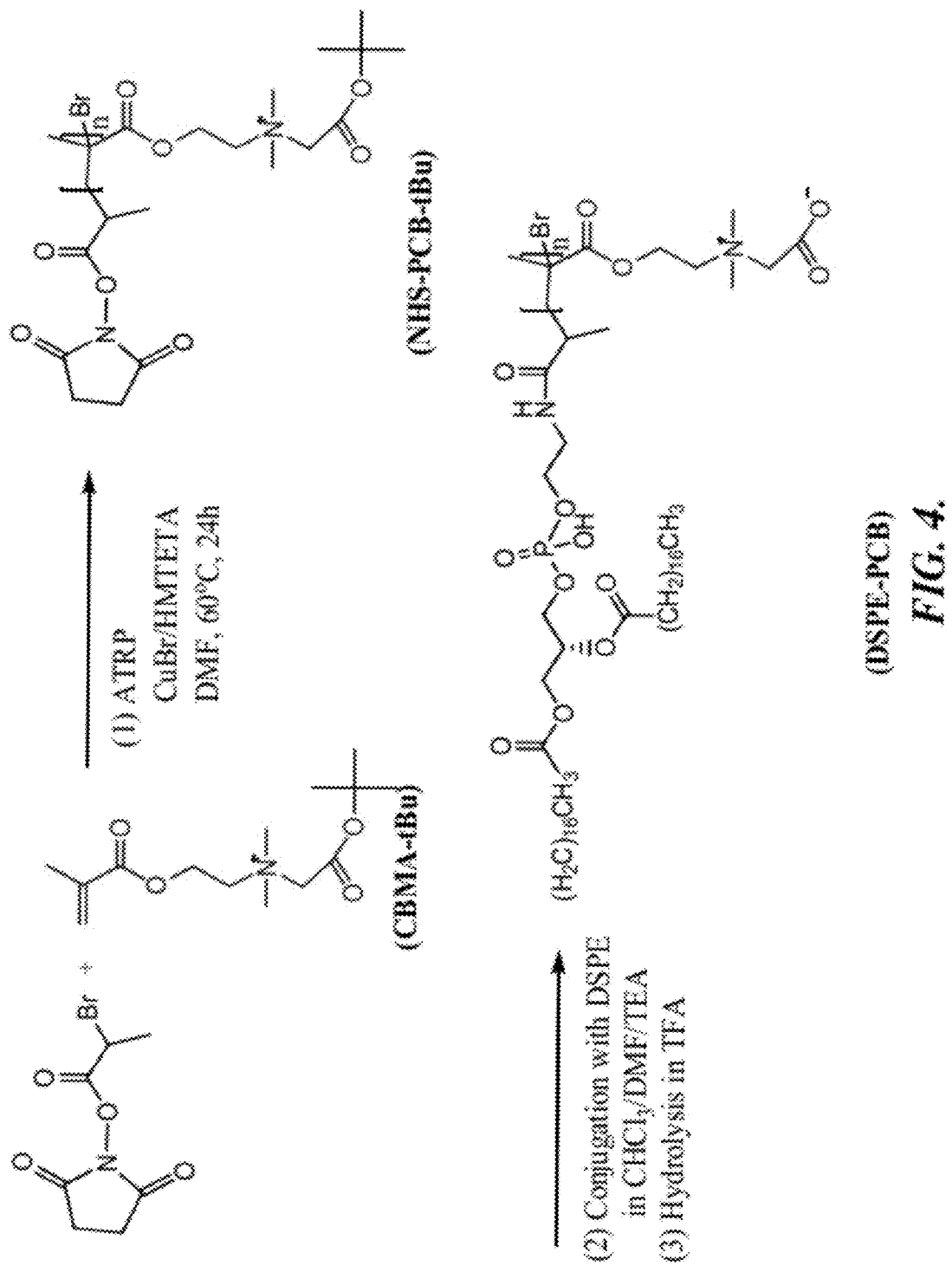
FIG. 4 is a schematic illustration of the preparation a representative zwitterionic block copolymer of the invention, DSPC-PCB.
Figure 5A:
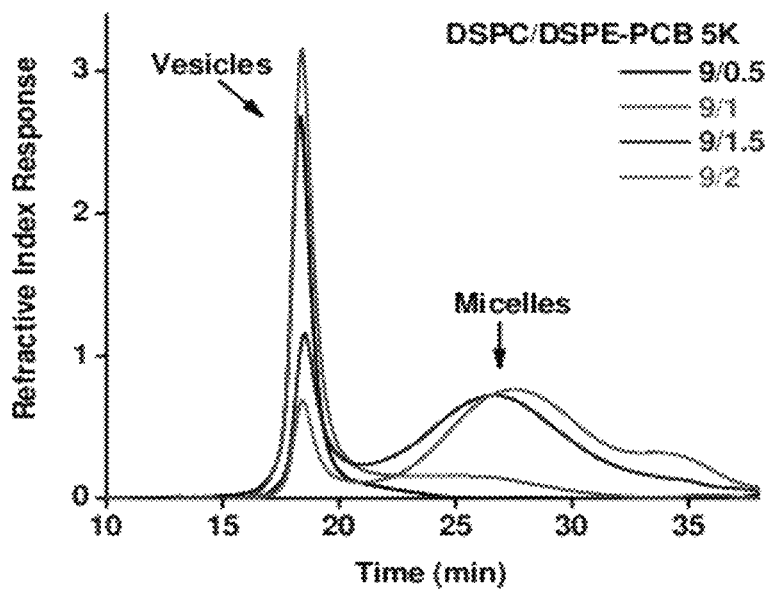
FIGS. 5A-5D compare size exclusion chromatography results as a function of molar composition for representative particles (vesicles and micelles) of the invention [DSPC/DSPE-PCB 5K (FIG. 5A); DSPC/DSPE-PCB 2K (FIG. 5B)] and related PEG particles [DSPC/DSPE-PEG 5K (FIG. 5C); DSPC/DSPE-PEG 2K (FIG. 5D)].
Figure 5B:
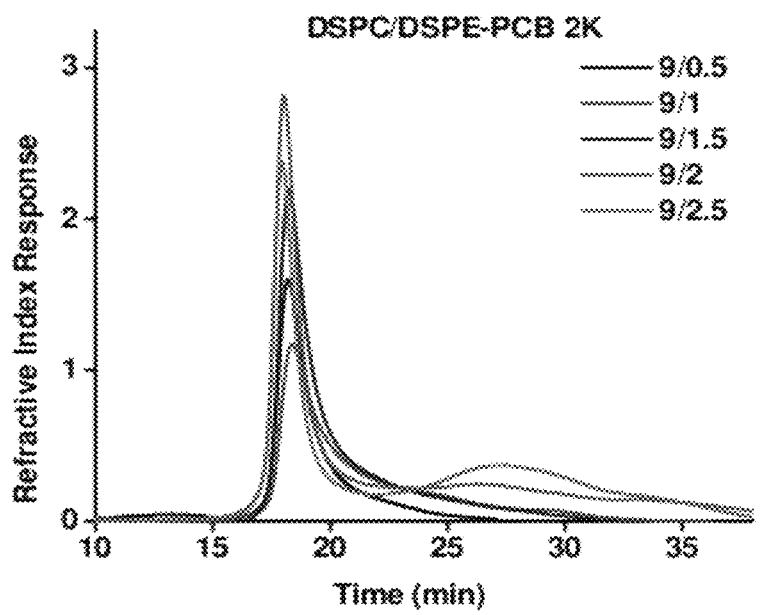
Figure 5C:
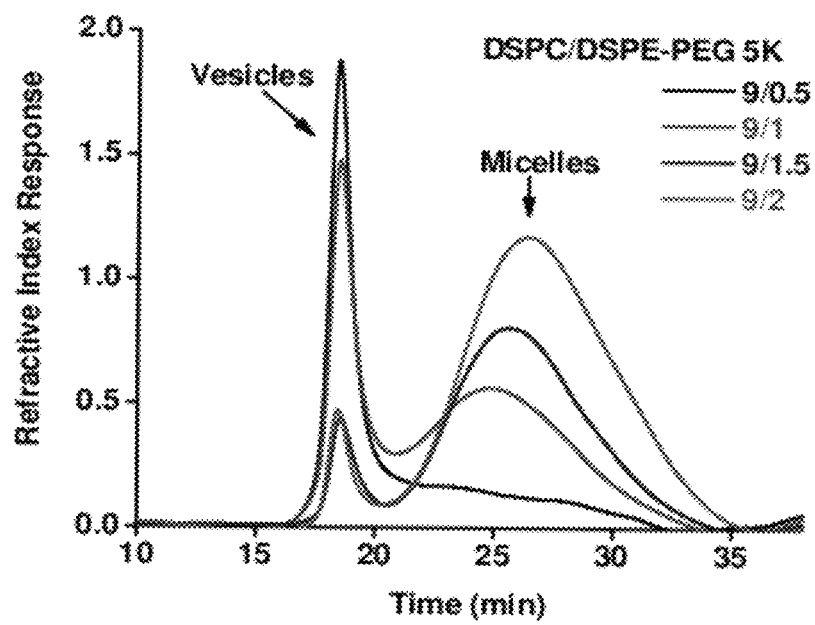
Figure 5D:
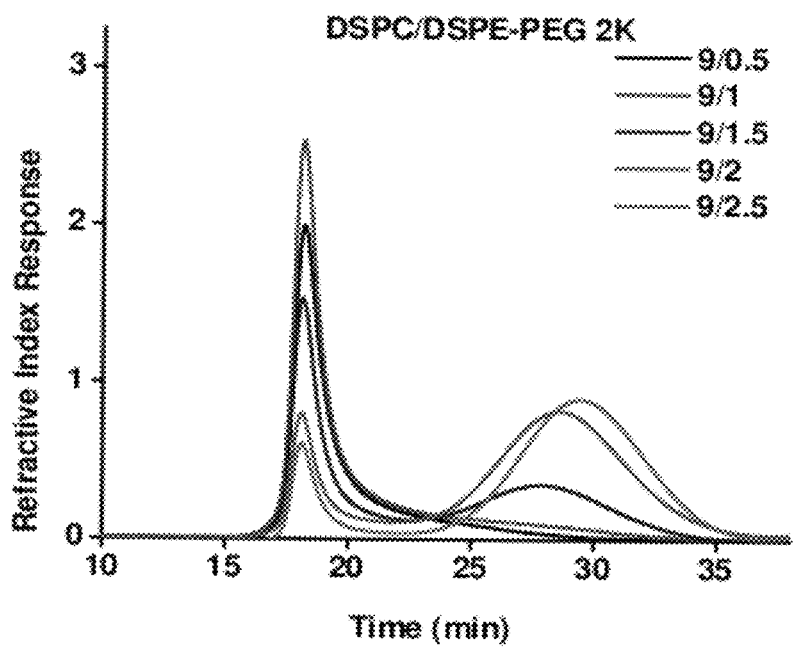

Preparation and Characteristics of a Representative Zwitterionic Conjugate DSPE-PCB In this example, the preparation and characteristics of a representative zwitterionic conjugate of the invention, DSPE-PCB, and related liposomes are described. The preparation of the conjugate is illustrated in FIG. 4.

DSPE-PCB Conjugate

NHS Ester Initiators (N-hydroxysuccinimide 2-bromopropanoate) for Atom Transfer Radical Polymerization (ATRP). N-Hydroxysuccinimide (2.26 G, 19.6 Mmol) and 2-bromopropionic acid (1.45 ml, 16.4 mmol) were dissolved in 500 ml of anhydrous dichloromethane in a round-bottomed flask, with a magnetic stirrer. The flask was cooled to 0° C. and a solution of N,N'-dicyclohexylcarbodiimide (3.35 g, 16.34 mmol) in dichloromethane (25 ml) was added dropwise. After stirring at room temperature overnight the reaction mixture was filtered and the solvent removed under reduced pressure to give a yellow solid. The product was further purified by flash chromatography. Obtained 2.4 g of white solid (9.63 mmol, yield=59%). $^1$H NMR (chloroform) δ (ppm): 1.97 and 2.00 (d, 3H, —COOCH(CH$_3$)Br), 2.89 (s, 4H, —COCH$_2$CH$_2$CO—), 4.64 (guar, J=6 Hz, 1H, —COOCH(CH$_3$)Br).

2-tert-Butoxy-N-(2-(methacryloyloxy)ethyl)-N,N-dimethyl-2-oxoethanaminium (CB-tBu). 5 g 2-(Dimethylamino)ethyl methacrylate and 8.68 g tert-butyl bromoacetate were reacted in 20 ml acetonitrile for 24 h at 50° C. under N$_2$ protection. Upon addition of 250 ml ethyl ether to the reaction mixture, the formed white crystals were isolated and dried. The resultng CB-tBu monomers were immediately stored in a dessicator at −20° C. (yield 96%). $^1$H NMR (D$_2$O) δ (ppm): 1.44 (s, 9H, —OC(CH$_3$)$_3$), 1.87 (s, 3H,CH$_2$=C(CH$_3$)COO—), 3.31 (s, 6H, —CH$_2$N(CH$_3$)$_2$CH$_2$COO—), 3.98 (t, J=3 Hz, 2H, CH$_2$=C(CH$_3$)COOCH$_2$CH$_2$N(CH$_3$)$_2$CH$_2$—), 4.28 (s, 2H, —CH$_2$N(CH$_3$)$_2$CH$_2$COO—), 4.60 (t, J=3 Hz, 2H, CH$_2$=C(CH$_3$)COOCH$_2$CH$_2$N(CH$_3$)$_2$CH$_2$—), 5.73 and 6.10 (s, 2H, CH$_2$=C(CH$_3$)COO—).

NHS-PCB-tBu. ATRP of CB-tBu was carried out in anhydrous dimethylformamide (DMF) using a Cu(I)Br/HMTETA catalyst. In a typical polymerization DMF and the liquid HMTETA ligand are separately purged of oxygen by bubbling with nitrogen. 1 g (3.67 mmol) of CB-tBu monomer and 125 mg (0.5 mmol) of NHS-initiator were added to a Schlenk tube. To a second Schlenk tube was added 71.7 mg (0.5 mmol) of Cu(I)Br. Both tubes were deoxygenated by cycling between nitrogen and vacuum three times. 8 and 2 mL of deoxygenated DMF were added to the monomer/initiator and Cu(I)Br tubes, respectively. 136 μL (0.50 mmol) of deoxygenated HMTETA was added to the Cu(I)Br containing solution and was stirred for 30 min under nitrogen protection. The catalyst solution (Cu(I)/HMTETA) was then all added to the monomer/initiator solution to start the reaction. The reaction was run overnight at room temperature. After polymerization, the reaction was fully precipitated in ethyl ether. The precipitate was then dried under vacuum and redissolved in minimal DMF (3-5 mL). This solution was vortexed until fully dissolved and precipitated in acetone to remove the soluble catalyst and trace monomer. This was repeated for a total of 3 times to fully remove the catalyst. The remaining ester polymer was dried overnight under vacuum and analyzed by NMR. (754 mg, yield=74.5%).

NHS-PCB and the Molecular Weight Measurement. NHS-PCB was obtained by hydrolysis of tBu Groups. 500 mg NHS-PCB-tBu was dissolved in 5 ml trifluoroacetic acid. This was allowed to sit for 2 hours. The solution was then precipitated in ethyl ether, dried overnight under vacuum. Molecular weight (e.g., around 4,909 Da) was determined from $^1$H NMR ($D_2O$) δ (ppm): 2.82 (s, 4H, —$COCH_2CH_2CO$— from the initiator), 3.27 (b, 6H, —$CH_2N(CH_3)_2CH_2COO^-$ from CBMA-1), 4.2 and 4.5 (m, 6H, —$COOCH_2CH_2N(CH_3)_2CH_2COO^-$). Note that free NHS will have $^1$H NMR ($D_2O$) δ (ppm): 2.67 (s, 4H, —$COCH_2CH_2CO$— from the initiator). Water phase GPC also shows MW=5410 Da with PDI=1.03. These MW data were used to characterize the MW for PCB block in DSPE-PCB.

DSPE-PCB. 1,2-distearoyl-sn-glycero-3-phosphoethanolamine (DSPE, Genzyme Pharmaceuticals) was used as received. $^1$H NMR (trifluoroacetic acid-d) δ (ppm): 0.907 (6H, t, J=6.3 Hz, —$CH_3$), 1.344 (56H, br s, $CH_3$—$(CH_2)_{14}$—), 1.752 (4H, m, $CH_3$—$(CH_2)_{14}$—$CH_2$—), 2.551 (4H, m, $CH_3$—$(CH_2)_{15}$—$CH_2$—), 3.664 (2H, s, —$CH_2$—$NH_3^+$), 4.438 and 4.606 (6H, m, —$CH_2$—CH($C_{17}H_{35}$COO)—$CH_2$—$PO_4$—$CH_2$—), 5.581 (1H, m, sn2-CH).

For a typical reaction, 120 mg NHS-PCB-tBu (MW for PCB is 5K) and 120 mg DSPE were stirred in 30 ml chloroform/4.3 ml DMF mixed solvents in the presence of 129 μl triethylamine for days. The reaction mixture was then evaporated and precipitated in ethyl ether. The precipitates was first extracted by acetonitrile and filtered. The filtrate was evaporated, treated by TFA for 4 h, precipitated in ethyl ether and vacuum dried. The dry product was neutralized in 200 mM phosphate buffer (pH=8) with 20 mM hydroxylamine, and gone through ultrofiltration (30K MW cutoff) in PBS followed in water repeatedly. Pure DSPE-PCB conjugates were retained in this process and freeze-dried. (yield=58%).

The formation of DSPE-PCB conjugation was confirmed and the molar ratio (DSPE/CB) was determined to be 1/20 by $^1$H NMR (trifluoroacetic acid-d) δ (ppm): 2.567 (m, 4H of $CH_3$—$(CH_2)_{15}$—$CH_2$— from DSPE), 4.637 (br m, 6H of —$CH_2$—CH($C_{17}H_{35}$COO)—$CH_2$—$PO_4$—$CH_2$— from DSPE, and 6H of —$COOCH_2CH_2N(CH_3)_2CH_2COO^-$ from PCB), 5.590 (s, 1H of sn2-CH from DSPE). This 1/20 (DSPE/CB) molar ratio implies roughly 5000 Da PCB conjugated to one DSPE molecule, in agreement with the molecular weight of unconjugated PCB determined via NMR and GPC methods.

DSPE-PCB Liposomes

Figure 6:
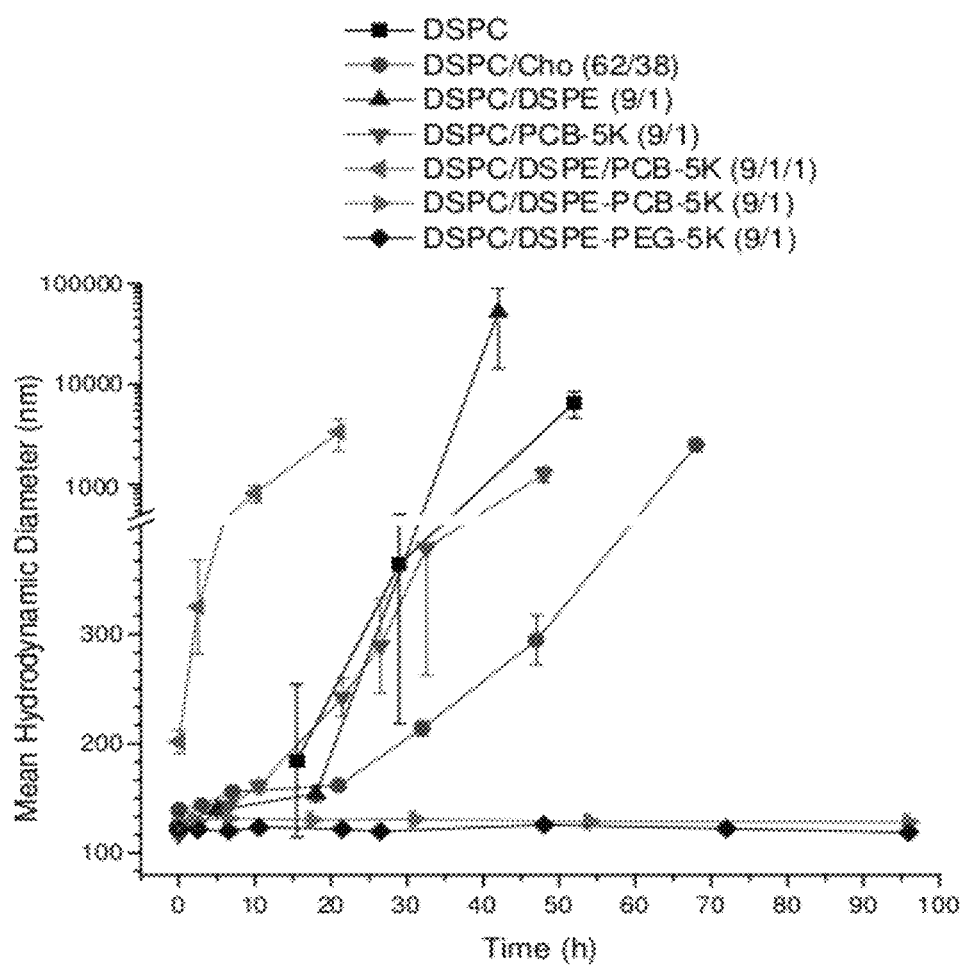
FIG. 6 compares liposome stability in PBS at 37° C. for a representative particle (liposome) of the invention (DSPC/DSPE-PCB 5K) to and related particles.

In a typical formulation, lipid components (e.g., including DSPC and DSPE-PCB or commercial DSPE-PEG) were mixed in 2,2,2-trifluoroethanol at desired molar ratio. A thin lipid film was formed by evaporation. Hydration of the lipid film was achieved by addition of PBS at 60° C. followed by 3 freeze-thaw cycles. The resulting liposomes were extruded 20 times through Avanti® Mini-Extruder at 60° C. equipped with a polycarbonate membrane (80 nm). Particle sizes and its polydispersity indexes (PDI) were measured in PBS, and zeta-potentials were measured in water. Typical liposome sizes and zeta-potentials for varied formulations are shown in FIGS. 5A-5D. Generally these liposomes were around 100 nm with low PDI numbers. These liposomes were analyzed through size exclusion chromatography (SEC) by a Waters Alliance 2695 Separations Module equipped with a Waters 2414 refractive index detector and a custom-built size exclusion column (Tricorn™ 10/600 Column packed with Sephacryl™ S-500 HR chromatography medium, GE Healthcare, Piscataway, N.J., USA). The mobile phase was PBS solution at a flow rate of 1 ml/min at 25° C. It should be noted that both DSPE-PCB and DSPE-PEG tested will form micelles alone in aqueous solution. A comparison of FIGS. 5A and 5B (DSPE-PCB) to FIGS. 5C and 5D (DSPE-PEG) indicates that within the same molecular weight, DSPE-PCB was able to incorporate more into the liposomes without leading to micellization. Liposomes were incubated in PBS at 37° C. to test their stability from aggregation. FIG. 6 shows only DSPE-PCB and DSPE-PEG conjugate modified liposomes were able to protect liposomes from long-term aggregation, while formulations lacking these conjugates started aggregating within few hours.

TABLE 1

Size and zeta-potential properties for different formulations.
5K or 2K represents the MW for the PCB or PEG polymers. Data were measured by triplicates and illustrated as mean value ± standard deviation.

| Liposomes (mol/mol) | Mean Diameter (nm) | PDI | Zeta-potential (mV) |
| --- | --- | --- | --- |
| DSPC/DSPE-PCB 5K (9/0.5) | 139.9 ± 1.778 | 0.084 ± 0.012 | −41.0 ± 0.100 |
| DSPC/DSPE-PCB 5K (9/1) | 127.5 ± 0.781 | 0.159 ± 0.008 | −42.7 ± 1.50 |
| DSPC/DSPE-PCB 5K (9/1.5) | 84.86 ± 0.4167 | 0.185 ± 0.007 | −40.6 ± 1.31 |
| DSPC/DSPE-PCB 5K (9/2) | 91.27 ± 4.456 | 0.284 ± 0.008 | −38.0 ± 0.651 |
| DSPC/DSPE-PCB 2K (9/0.5) | 115.3 ± 3.322 | 0.145 ± 0.033 | −32.9 ± 3.68 |
| DSPC/DSPE-PCB 2K (9/1) | 103.2 ± 2.997 | 0.121 ± 0.033 | −43.3 ± 3.11 |
| DSPC/DSPE-PCB 2K (9/1.5) | 104.9 ± 1.223 | 0.084 ± 0.017 | −43.4 ± 1.14 |
| DSPC/DSPE-PCB 2K (9/2) | 122.6 ± 0.9252 | 0.132 ± 0.027 | −48.6 ± 2.40 |
| DSPC/DSPE-PEG 5K (9/0.5) | 160.4 ± 3.444 | 0.021 ± 0.013 | −20.3 ± 3.61 |
| DSPC/DSPE-PEG 5K (9/1) | 122.2 ± 0.7234 | 0.239 ± 0.012 | −16.5 ± 1.74 |
| DSPC/DSPE-PEG 5K (9/1.5) | 92.81 ± 3.010 | 0.362 ± 0.014 | −16.5 ± 0.603 |
| DSPC/DSPE-PEG 5K (9/2) | 96.14 ± 0.5859 | 0.401 ± 0.009 | −13.8 ± 0.252 |
| DSPC/DSPE-PEG 2K (9/0.5) | 132.0 ± 6.622 | 0.195 ± 0.018 | −26.9 ± 0.451 |
| DSPC/DSPE-PEG 2K (9/1) | 129.2 ± 5.027 | 0.083 ± 0.075 | −31.8 ± 1.40 |
| DSPC/DSPE-PEG 2K (9/1.5) | 136.3 ± 10.21 | 0.129 ± 0.103 | −33.2 ± 0.404 |
| DSPC/DSPE-PEG 2K (9/2) | 102.5 ± 6.271 | 0.280 ± 0.031 | −32.3 ± 1.46 |
| DSPC/DSPE-PEG 2K (9/2.5) | 121.0 ± 4.709 | 0.296 ± 0.047 | −30.8 ± 0.964 |

In Vivo Circulation Studies on DSPE-PCB Liposomes. All the liposomes listed in Table 2 are labeled fluorescently by adding 1 mol % 1,2-dioleoyl-sn-glycero-3-phosphoethanolamine-N-(lissamine rhodamine B sulfonyl) (Avanti) during the liposome formulation processes. All these liposomes formulation are below 150 nm with nearly monopolydispersity. These formulations are evaluated on rats for their circulation profiles. Sprague Dawley (150 g) rats were randomly divided into groups (group size is 3) and anesthetized with 3-5% isofluran. 200 μl of each liposome formulation containing 2.3 μmol phospholipids was injected through the tail vein. At 5 min, 4 h, 8 h, 24 h, and 48 h, the rat was anesthetized with 3-5% isofluran temporarily and 50-100 μl blood was drawn from either left or right sophenous vein. After 48 h, rats were euthanized by $CO_2$ inhalation. The blood collected will be weighted and mixed with water/acetonitrile cocktails. After brief centrifugation, the supernatants will be measured for fluorescent emission at 583.6 nm with the excitation at 557 nm. Calibration curves were established to quantify the doses of liposomes in these blood samples. The dose data vs. the time were fitted by a one-compartment pharmacokinetic model and the circulation half-life and area under the curve (AUC) data were calculated and shown in Table 3. Significant longer circulation of DSPE-PCB liposomes was observed than DSPE-PEG counterparts. Such as DSPC/DSPE-PCB 5K (9/1) has a half-life of 9-10 hours, much longer than DSPC/DSPE-PEG 5K (9/1) which is 3-4 hours.

TABLE 2

Size and zeta-potential properties for different formulations.
5K or 2K represents the MW for the PCB or PEG polymers. Data were measured by triplicates and illustrated as mean value ± standard deviation.

| Liposomes Formulation (mol/mol) | Mean Diameter (nm) | PDI | Zeta-potential (mV) |
|---|---|---|---|
| DSPC | 119.3 ± 3.474 | 0.105 ± 0.015 | −18.0 ± 2.26 |
| DSPC/DSPE-PCB 2K (9/1) | 144.0 ± 0.6245 | 0.106 ± 0.016 | −45.3 ± 0.577 |
| DSPC/DSPE-PEG 2K (9/1) | 127.8 ± 0.7095 | 0.135 ± 0.011 | −35.9 ± 0.173 |
| DSPC/DSPE-PCB 2K (9/1.5) | 112.6 ± 2.756 | 0.062 ± 0.023 | −46.8 ± 0.808 |
| DSPC/DSPE-PEG 2K (9/1.5) | 97.38 ± 2.847 | 0.081 ± 0.013 | −32.5 ± 1.81 |
| DSPC/DSPE-PCB 5K (9/0.47) | 104.9 ± 2.489 | 0.053 ± 0.019 | −36.8 ± 0.306 |
| DSPC/DSPE-PEG 5K (9/0.47) | 113.6 ± 4.284 | 0.041 ± 0.014 | −16.8 ± 0.985 |
| DSPC/DSPE-PCB 5K (9/1) | 98.31 ± 1.442 | 0.087 ± 0.009 | −37.5 ± 0.300 |
| DSPC/DSPE-PEG 5K (9/1) | 120.6 ± 2.169 | 0.063 ± 0.015 | −17.4 ± 1.10 |

TABLE 3

In vivo circulation profiles for different formulations.
5K or 2K represents the MW for the PCB or PEG polymers. Data were measured by triplicates and illustrated as mean value ± standard deviation.

| Liposome Formulation (mol/mol) | Half-Life (h) | AUC (% ID h) |
|---|---|---|
| DSPC | 0.70 ± 0.04 | 108.73 ± 5.97 |
| DSPC/DSPE-PCB 2K (9/1) | 3.09 ± 0.10 | 462.28 ± 14.67 |
| DSPC/DSPE-PEG 2K (9/1) | 2.25 ± 0.10 | 330.46 ± 12.97 |
| DSPC/DSPE-PCB 2K (9/1.5) | 6.60 ± 0.62 | 982.82 ± 104.92 |
| DSPC/DSPE-PEG 2K (9/1.5) | 4.05 ± 0.18 | 588.75 ± 26.54 |
| DSPC/DSPE-PCB 5K (9/0.47) | 5.55 ± 0.30 | 830.90 ± 51.31 |
| DSPC/DSPE-PEG 5K (9/0.47) | 4.36 ± 0.06 | 633.51 ± 11.63 |
| DSPC/DSPE-PCB 5K (9/1) | 9.56 ± 1.58 | 1489.07 ± 276.98 |
| DSPC/DSPE-PEG 5K (9/1) | 3.74 ± 0.23 | 534.84 ± 34.20 |

% ID represents % injected dose.

EXAMPLE 2

Preparation and Characteristics of a Representative Nanoparticle Drug Delivery System Amphiphilic PLGA Zwitterionic Block Copolymers In this example, the preparation and characteristics of a representative nanoparticle drug delivery system of the invention are described.

Materials. 2-bromoisobutyryl bromide, t-Boc-aminoethyl alcohol, 2-(dimethylamino)ethyl methacrylate, tert-butyl bromoacetate, Cu(I)Br, 1,1,4,7,10,10-hexamethyltriethyl-enetetramine (HMTETA), N-(3-dimethylaminopropyl)-N'-ethylcarbodiimide hydrochloride (EDC), 2,2,2-trifluoroethanol (TFE), and 4-aminophenyl β-D-galactopyranoside (NH2-galactose) were purchased from Sigma-Aldrich, St. Louis, Mo. Trifluoroacetic acid (TFA) and N-hydroxysuccinimide (NHS) were purchased from Acros Organics USA, Morris Plains, N.J. Poly(D,L-lactide-co-glycolide) (PLGA) with a 50:50 monomer ratio were purchased from Durect Corporation, Pelham, Ala. Docetaxel (Dtxl) was purchased from LC Laboratories, Woburn, Mass. 5-(Aminomethyl) fluorescein hydrochloride, and 22-(N-(7-nitrobenz-2-oxa-1, 3-diazol-4-yl)amino)-23,24-bisnor-5-cholen-3β-ol (NBD) were purchased from Invitrogen, Carlsbad, Calif.

Nanoparticle Preparation

2-Aminoethyl 2-Bromoisobutyrate. The ATRP initiators with $NH_2$ functional groups were synthesized as follows. Briefly, 3.57 g 2-bromoisobutyryl bromide was added to a solution of 2.5 g t-Boc-aminoethyl alcohol and 1.73 g triethylamine in 8 ml methylene chloride in an ice bath. After 4 h reaction, the salts were filtered off and the filtrate was extracted with saturated sodium bicarbonate solution. Methylene chloride phase was dried over magnesium sulfate and evaporated. The resulting t-Boc-aminoethyl 2-bromoisobutyrate was treated by 15 ml trifluoroacetic acid (TFA) for 2 h and crystallized upon addition of ethyl ether (yield 95%). $^1$H NMR (DMSO-$d_6$) δ (ppm): 1.93 (s, 6H, —C(CH$_3$)$_2$Br), 3.16 (s, 2H, TFA$^-$.NH$_3^+$CH$_2$CH$_2$OCO), 4.31 (t, J=5 Hz, 2H, TFA$^-$.NH$_3^+$CH$_2$CH$_2$OCO), 8.22 (s, 3H, TFA$^-$.NH$_3^+$CH$_2$CH$_2$OCO).

2-tert-butoxy-N-(2-(methacryloyloxy)ethyl)-N,N-dimethyl-2-oxoethanaminium (CB-tBu monomer). 5 g 2-(Dimethylamino)ethyl methacrylate and 8.68 g tert-butyl bromoacetate were reacted in 20 ml acetonitrile for 24 h at 50° C. under $N_2$ protection. Upon addition of 250 ml ethyl ether to the reaction mixture, the formed white crystals were isolated and dried. The resulting CB-tBu monomers were immediately stored in a desiccator at −20° C. (yield 96%). $^1$H NMR ($D_2O$) δ (ppm): 1.44 (s, 9H, —OC(CH$_3$)$_3$), 1.87 (s, 3H, CH$_2$═C(CH$_3$)COO—), 3.31 (s, 6H, —CH$_2$N(CH$_3$)$_2$CH$_2$COO—), 3.98 (t, J=3 Hz, 2H, CH$_2$═C(CH$_3$)COOCH$_2$CH$_2$N(CH$_3$)$_2$CH$_2$—), 4.28 (s, 2H, —CH$_2$N(CH$_3$)$_2$CH$_2$COO—), 4.60 (t, J=3 Hz, 2H, CH$_2$═C(CH$_3$)COOCH$_2$CH$_2$N(CH$_3$)$_2$CH$_2$—), 5.73 and 6.10 (s, 2H, CH$_2$═C(CH$_3$)COO—).

Synthesis of PCB-tBu Polymers. The ATRP of CB-tBu monomers was carried out as follows: 74 mg Cu(I)Br and 148.6 mg HMTETA were placed into a Schlenk tube and underwent three vacuum-nitrogen cycles. Then, 7 ml degassed DMF was added to make solution A. Similarly, 1.8 g CB-tBu monomers and 80 mg 2-aminoethyl 2-bromoisobutyrate were placed into another Schlenk tube with oxygen fully excluded, followed by addition of 8 ml degassed DMF to make solution B. Polymerization was started by transferring solution B into solution A under $N_2$ protection. After reaction at 60° C. for 24 h, the polymers were first precipitated in ethyl ether, then were dissolved in a small amount of ethanol and precipitated in acetone repeatedly to remove residual monomers, initiators and catalysts. The resulting PCB-tBu was dried under vacuum before further use.

PLGA-b-PCB-tBu Conjugation. The conjugation process was via NHS/EDC chemistry. Briefly, 3.2 g COOH terminated PLGA (0.20 dl/g), 86.4 mg NHS and 147.2 mg EDC were reacted in 6 ml methylene chloride for 4 h at room temperature. Then, 5 ml ethyl ether was added to obtain white precipitates. The resulting PLGA-NHS was washed with cold ethyl ether/methanol mixture (2/1, v/v) to remove any NHS and EDC residuals, then vacuum-dried before use. $TFA^-$.$NH_3^+$-terminated pCBMA-tBu was treated with an excess of triethylamine to remove TFA protection. $NH_2$-terminated pCBMA-tBu was purified via filtration, precipitated into ethyl ether, and vacuum-dried. 878 mg $NH_2$-terminated PCB-tBu and 1.68 g PLGA-NHS were conjugated in the presence of 50 μl triethylamine in 7 ml acetonitrile at 60° C. for 20 h. The resulting PLGA-PCB-tBu was precipitated in cold methanol. PCBMA-tBu contaminant was removed by repeating the washing cycle. The formation of PLGA-PCBMA-tBu conjugation was confirmed and the weight ratio (PLGA/PCB) was determined to be 6/1 (mole ratio 12.4/1) by $^1$H NMR (Acetonitrile-$d_3$) δ (ppm): 1.55 (m, 3H, —COCH($CH_3$)O—, in PLGA, and 9H, —OC($CH_3$)$_3$ in PCB-tBu), 3.65 (br, 6H, —$CH_2$N($CH_3$)$_2$$CH_2$COOC($CH_3$)$_3$, in PCB-tBu), 4.85 (m, 2H, —COCH$_2$O—, in PLGA), 5.22 (m, 1H, —COCH($CH_3$)O—, in PLGA). The polymers were dried in vacuum before use.

Hydrolysis of tBu Ester Groups. In control experiments, PLGA treated with TFA for up to 6 h did not show significant molecular weight changes, and PCB-tBu after 1 h TFA treatment showed no signal at 1.44 ppm in $^1$H NMR ($D_2O$) indicating that tBu ester groups are fully removed. To confirm that ester bonds at methacrylates were not destroyed following the TFA treatment, CB-tBu monomers were hydrolyzed in TFA for 1 h and the hydrolyzed product identified as CB zwitterionic monomers by $^1$H NMR ($D_2O$) δ (ppm): 1.89 (s, 3H, $CH_2$=C($CH_3$)COO—), 3.31 (s, 6H, —$CH_2$N($CH_3$)$_2$$CH_2$COO—), 3.98 (t, J=3 Hz, 2H, $CH_2$=C($CH_3$)COOCH$_2$$CH_2$N($CH_3$)$_2$$CH_2$—), 4.48 (s, 2H, —$CH_2$N($CH_3$)$_2$$CH_2$COO$^-$), 4.54 (s, 2H, $CH_2$=C($CH_3$)COOCH$_2$$CH_2$N($CH_3$)$_2$$CH_2$—), 5.75 and 6.06 (s, 2H, $CH_2$=C($CH_3$)COO—). To obtain PLGA-co-PCB, PLGA-co-PCB-tBu was treated with TFA for 1 h to remove tBu ester groups. The resulting PLGA-co-PCB was precipitated into ethyl ether, and re-dissolved in a small amount of TFE and precipitated in ethyl ether repeatedly. After vacuum dry, the copolymers are ready for NP formulation. Weight ratio (PLGA/PCB) was determined to be 10/1 by $^1$H NMR (trifluoroacetic acid-d) δ (ppm): 5.50 (m, 1H, —COCH($CH_3$)O—, in PLGA), 5.10 (m, 2H, —COCH$_2$O—, in PLGA), 1.77 (d, 3H, —COCH($CH_3$)O—, in PLGA), 3.64 (br, 6H, —$CH_2$N($CH_3$)$_2$$CH_2$COO—, in PCB).

The molecular weight and distribution of PCB homopolymers (derived by hydrolysis of PCB-tBu polymers) are determined by a Waters Alliance 2695 Separations Module equipped with a Waters Ultrahydrogel 1000 column and a Waters 2414 reflex detector. The mobile phase was 100 mM NaCl aqueous solution at a flow rate of 0.7 ml/min at 35° C. Poly(ethylene oxide) from Polymer Laboratories were used as standards. Gel permeation chromatography shows a molecular weight (Mn) of 13640 with polydispersity of 1.12.

Formulation of PLGA-PCB NPs. Solvent displacement (nanoprecipitation) method was used to formulate NPs. PLGA-PCB copolymers were dissolved in TFE/MeOH 1/1 v/v cosolvent at the concentration of 0.5 mg/ml. Water (water:organic solvent volume ration, 4:1) was transferred to copolymer solution in a dropwise manner under 1000 rpm stir. After 2 h, solvents were exchanged to PBS and resulting PLGA-PCB NPs were concentrated to the desired concentration by an Amicon Ultra-4 centrifugal filter (Millipore, Billerica, Mass., US) with 100,000 Da MW cutoff. PLGA NPs were prepared as described in J. Cheng, B. A. Teply, I. Sherifi, J. Sung, G. Luther, F. X. Gu, E. Levy-Nissenbaum, A. F. Radovic-Moreno, R. Langer, o. C. Farokhzad, Biomaterials 2007, 28, 869. Docetaxel was loaded in the NPs by mixing with polymers in the organic solvent and followed the above-mentioned procedures to formulate PLGA-PCB/Dtxl NPs. The mean diameter, polydispersity index (PDI) and zeta-potential of NPs were determined by Zetasier Nano-ZS (Malvern Instruments Ltd, Malvern, WR, UK) in triplicates. PDI ranging from 0 to 1.00 was used to characterize the NP size distribution. NPs are considered as monodisperse when PDI<0.10.

Drug Loading and Releasing Kinetics. After nanoprecipitation of polymers (either PLGA or PLGA-PCB) with docetaxel, preparation solution containing drug-loaded NPs and free drugs went through a Microcon centrifugal filter (Millipore, Billerica, Mass.) with 100,000 Da MW cutoff. The drug content in the filtrates (containing free drugs) along with the preparation solution were compared to determine the drug loading (drug/polymers, w/w). In drug releasing studies, Dtxl-loaded NP solutions were placed into Slide-A-Lyzer MINI dialysis microtubes (3500 Da MW cutoff, Pierce, Rockford, Ill.) at 100 μl (0.33 mg/ml) per tube. Those tubes were dialyzed against 1 L PBS at 37° C. with gentle stirring. PBS was refreshed every 24 h. At varied time points, three microtubes were taken to determine drug content retained by the NPs. All aqueous samples were mixed with equal-volume acetonitrile overnight to fully release the drug before running HPLC. Docetaxel content was quantified in triplicates by a Waters Alliance 2695 Separations Module equipped with a reverse-phase C18 column (Econosil, 250×4.6 mm, 5 μm, Alltech, Deerfield, Ill., USA) and a UV detector (wavelength of 227 nm). The mobile phase was water and acetonitrile (v/v 50/50) at a flow rate of 0.5 ml/min at room temperature. The retention time for free Doc was 13.75 min.

PLGA-PCB NP Functionalization with Dye Molecules and Targeting Ligands.

Molecules of interest can be immobilized onto PLGA-PCB NPs via EDC/NHS chemistry. To conjugate dye molecules, NPs were incubated with 400 mM EDC and 200 mM NHS in water for 20 min, and washed with pure water to remove unreacted EDC and NHS. 0.5 mg NHS-activated NPs in 100 μl water were reacted with 25 μl of 5-(aminomethyl)fluorescein hydrochloride (Invitrogen, Carlsbad, Calif., US) at the concentration of 10 mg/ml in 10 mM sodium borate buffer, pH=9 at dark place for 2.5 h. The resulting dye-NP conjugates were washed with pH 9 buffer and water, resuspended in water, and analyzed with the FACScan flow cytometer (Becton Dickinson, San Jose, Calif.) at the concentration of 0.5 mg/ml. For the immobilization of targeting ligands, 22-(N-(7-nitrobenz-2-oxa-1,3-diazol-4-yl)amino)-23,24-bisnor-5-cholen-3β-ol (NBD) was formulated into PLGA-PCB NPs with initial drug loading of 0.25 wt %. The resulted PLGA- PCB/NBD NPs were activated by 400 mM EDC and 200 mM NHS in water for 20 min. 0.5 mg NHS-activated NPs in 100 μl water were reacted with 10 μl of NH₂-galactose at the concentration of 25 mg/ml in 10 mM sodium borate buffer, pH=9 for 1 h. The resulting galactose-NP conjugates were washed with pH 9 buffer and PBS, and resuspended in PBS before cell incubation. HepG2 cells were grown in 24-well plates in full MEM medium (Hyclone, Logan, Utah) supplemented with non-essential amino acid, sodium pyruvate and 10% fetal bovine serum (FBS) under 5% CO₂ at 37° C. to allow 50% confluence. Cells were then washed with pre-warmed PBS and incubated with 400 μl/well NP-containing MEM medium without FBS supplement (PLGA-PCB/NBD-Galactose NP concentration: 1.25 mg/ml). After 2 h, cells were washed with PBS and supplemented with 400 μl/well FBS-containing medium. After 20 h incubation at 37° C., cells were visualized using a Nikon TE2000 U microscope. For control experiments, EDC was absence while all other conditions and procedures were exactly the same.

Cytotoxicity Assays for PLGA-PCB NPs. The cytotoxicity of the NPs was evaluated using a Vybrant® MTT Cell Proliferation Assay Kit (Molecular Probes, Eugene, Oreg.). Briefly, HepG2 cells were grown in 96-well plates in full MEM medium supplemented with non-essential amino acid, sodium pyruvate and 10% FBS under 5% CO₂ at 37° C. to allow 80-90% confluence. For each well, cells were washed with PBS and incubated with 200 μl full medium containing varied concentration of either PLGA-PCB or PLGA NPs for 24 h. Cells were washed with PBS to remove NPs and incubated with 100 μl full medium plus 50 μl of 12 mM MTT stock solution for another 4 h. Then, MTT-containing medium was replaced with 150 μl DMSO to dissolve the formed crystal at 37° C. for 10 min. Absorbance (Abs) was measured at 570 nm using a SpectraMax M5 microplate reader (Molecular Devices, Sunnyvale, Calif.) with pure DMSO as the blank reading. Cells with no NP incubation were used as the controls and cell viability upon NPs treatment was estimated in triplicate: cell viability (%)=Abs$_{sample}$/Abs$_{control}$×100.

While illustrative embodiments have been illustrated and described, it will be appreciated that various changes can be made therein without departing from the spirit and scope of the invention.

The embodiments of the invention in which an exclusive property or privilege is claimed are defined as follows:

1. A zwitterionic conjugate, comprising a vesicle-forming lipid covalently coupled to a poly(carboxybetaine), a poly(sulfobetaine), or a poly(phosphobetaine), wherein the poly(carboxybetaine), poly(sulfobetaine), or poly(phosphobetaine) comprises a plurality of repeating units, each repeating unit having the formula:

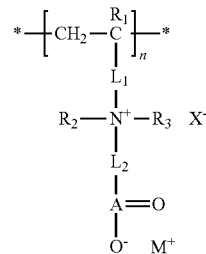

wherein
$R_1$ is selected from the group consisting of hydrogen, fluorine, trifluoromethyl, $C_1$-$C_6$ alkyl, and $C_6$-$C_{12}$ aryl groups;
$R_2$ and $R_3$ are independently selected from the group consisting of alkyl and aryl, or taken together with the nitrogen to which they are attached form a cationic center;
$L_1$ is a linker that covalently couples the cationic center [$N^+(R_2)(R_3)$] to the polymer backbone [—($CH_2$—$CR_1$)$_n$—];
$L_2$ is a linker that covalently couples the anionic center [A(=O)O⁻] to the cationic center; A is C, S, SO, P, or PO;
$M^+$ is a counter ion associated with the (A=O)O⁻ anionic center; $X^-$ is a counter ion associated with the cationic center; and n is an integer from 1 to about 10,000.

2. The conjugate of claim 1, wherein the lipid is distearoyl phosphatidylethanolamine (DSPE).

3. An assembly, comprising a plurality of conjugates of claim 1.

4. The assembly of claim 3 in the form of a micelle, a liposome, or a polymerosome.

5. A composition, comprising the assembly of claim 3 and a pharmaceutically accepted carrier or diluent.

6. The conjugate of claim 1, wherein the lipid is a phospholipid, a sphingolipid, or a sterol.

7. The conjugate of claim 1, wherein the lipid is a diacylphosphatidylethanolamine, a ceramide, a sphingomyelin, a dihydrosphingomyelin, a cephalin, or a cerebroside.

8. The conjugate of claim 1, wherein the lipid is a phosphatidylethanolamine (PE), a phosphatidylglycerol (PG), aphosphatidic acid (PA), or a phosphatidylinositol (PI).

9. The conjugate of claim 1, wherein the lipid is dioleoylphosphatidylglycerol (DOPG), dipalmitoylphosphatidylglycerol (DPPG), dioleoyl-phosphatidylethanolamine (DOPE), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, 1-stearoyl-2-oleoyl-phosphatidyethanolamine (SOPE), or 1,2-dioleoyl-sn-glycero-3-phophoethanolamine (transDOPE).

* * * * *